United States Patent
White et al.

(10) Patent No.: US 10,644,468 B2
(45) Date of Patent: *May 5, 2020

(54) MEDICAL LEAD CONNECTORS WITH CONTACT ELECTRODES

(71) Applicant: BENCHMARK ELECTRONICS, INC., Rochester, MN (US)

(72) Inventors: Robert Raymond White, Rochester, MN (US); Daniel William Johns, Rochester, MN (US); Daniel Patrick Higgins, Rochester, MN (US)

(73) Assignee: BENCHMARK ELECTRONICS, INC., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,858

(22) Filed: Nov. 2, 2018

(65) Prior Publication Data

US 2019/0074644 A1   Mar. 7, 2019

Related U.S. Application Data

(63) Continuation-in-part of application No. 15/980,533, filed on May 15, 2018, which is a continuation-in-part
(Continued)

(51) Int. Cl.
*H01R 24/58* (2011.01)
*A61N 1/375* (2006.01)
(Continued)

(52) U.S. Cl.
CPC ........... *H01R 24/58* (2013.01); *A61N 1/3752* (2013.01); *H01R 13/02* (2013.01); *H01R 12/59* (2013.01);
(Continued)

(58) Field of Classification Search
CPC .... H01R 24/58; H01R 12/59; H01R 2201/12; H01R 13/2414; H01R 43/20;
(Continued)

(56) References Cited

U.S. PATENT DOCUMENTS 2,767,383 A   10/1956  Killian
3,848,223 A *  11/1974  Pechard ............... H01R 12/721
                                                                     439/637
(Continued)

FOREIGN PATENT DOCUMENTS

EP        1085619      3/2001
JP       57-15374      1/1982
(Continued)

OTHER PUBLICATIONS

Extended European Search Report for European Patent Application No. 18180869.2, dated Nov. 13, 2018 (5 pages).
(Continued)

*Primary Examiner* — Travis S Chambers
(74) *Attorney, Agent, or Firm* — Sheppard, Mullin, Richter & Hampton LLP

(57) ABSTRACT

Embodiments disclosed herein include devices and methods pertaining to medical lead connectors. According to various embodiments of the disclosed technology, disclosed is a lead connector that may include a base member; a flexible circuit disposed on the base member and including a plurality of electrical contacts; a plurality of contacts positioned to allow contact between a lead inserted into the lead connector and the plurality of contacts and between the plurality of contacts and the plurality of electrical contacts of the flexible circuit; and a casing that includes a bottom casing and a cover member. When a lead is inserted into the lead connector via an opening on the cover member, the lead may push against the plurality of contacts, electrically coupling
(Continued)

the lead to the flexible circuit via the plurality of contacts and the plurality of electrical contacts of the flexible circuit.

22 Claims, 15 Drawing Sheets

Related U.S. Application Data of application No. 15/640,419, filed on Jun. 30, 2017, now Pat. No. 9,972,951.

(51) Int. Cl.
*H01R 13/02* (2006.01)
*H01R 12/59* (2011.01)
*H01R 12/81* (2011.01)
*H01R 13/24* (2006.01)

(52) U.S. Cl.
CPC .......... *H01R 12/81* (2013.01); *H01R 13/2478* (2013.01); *H01R 2201/12* (2013.01)

(58) Field of Classification Search
CPC .. H01R 2107/00; H01R 12/81; H01R 12/714; H01R 13/22; H01R 13/24; H01R 13/2407; H01R 13/2421; A61N 1/3752
USPC .................................. 439/669, 67, 289, 909
See application file for complete search history.

(56) References Cited

U.S. PATENT DOCUMENTS

| | | | |
|---|---|---|---|
| 5,070,605 | A | 12/1991 | Daglow |
| 6,662,035 | B2 | 12/2003 | Sochor |
| 6,671,534 | B2 | 12/2003 | Putz |
| 8,162,684 | B1 | 4/2012 | Sochor |
| 8,593,816 | B2 * | 11/2013 | Iyer ...................... A61N 1/3754 |
| | | | 361/306.2 |
| 9,972,951 | B1 * | 5/2018 | White .................. A61N 1/3752 |
| 2002/0095079 | A1 * | 7/2002 | Putz .......................... A61B 5/04 |
| | | | 600/378 |
| 2002/0175695 | A1 | 11/2002 | Ahmann |
| 2008/0009192 | A1 * | 1/2008 | Kast ..................... A61N 1/3752 |
| | | | 439/607.41 |
| 2008/0274651 | A1 | 11/2008 | Boyd |

FOREIGN PATENT DOCUMENTS

| | | |
|---|---|---|
| WO | 03061469 | 7/2003 |
| WO | 2007109762 | 9/2007 |

OTHER PUBLICATIONS

Extended European Search Report dated Mar. 17, 2020 for European Application No. 19206765.5.

* cited by examiner

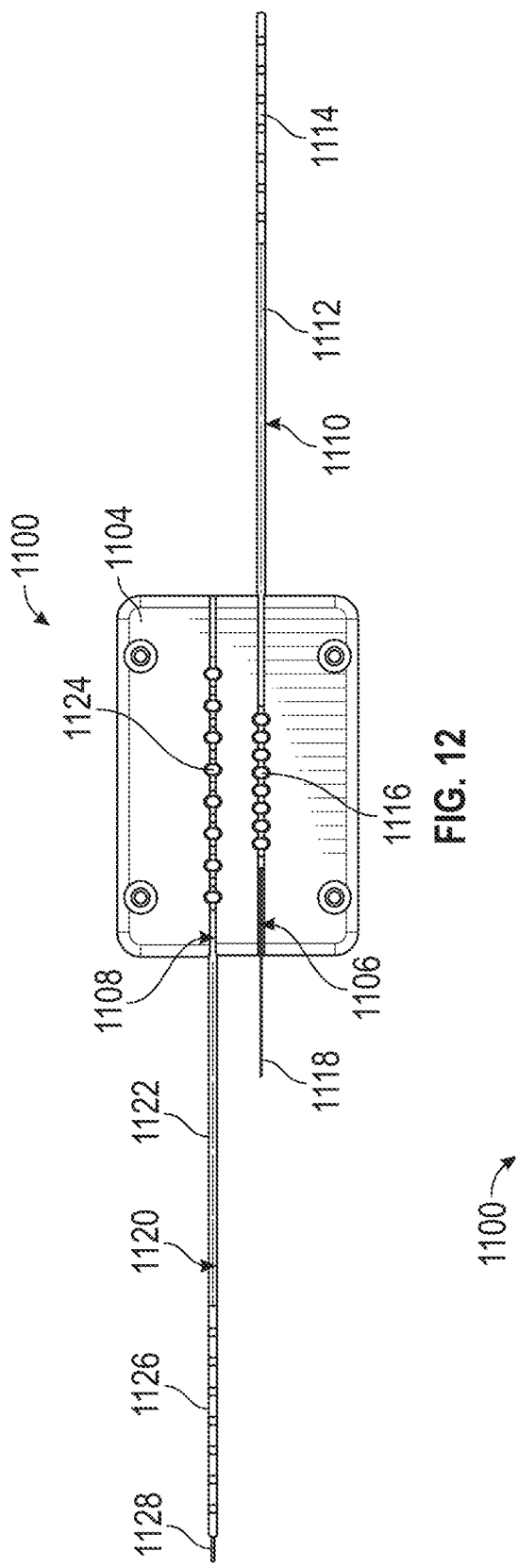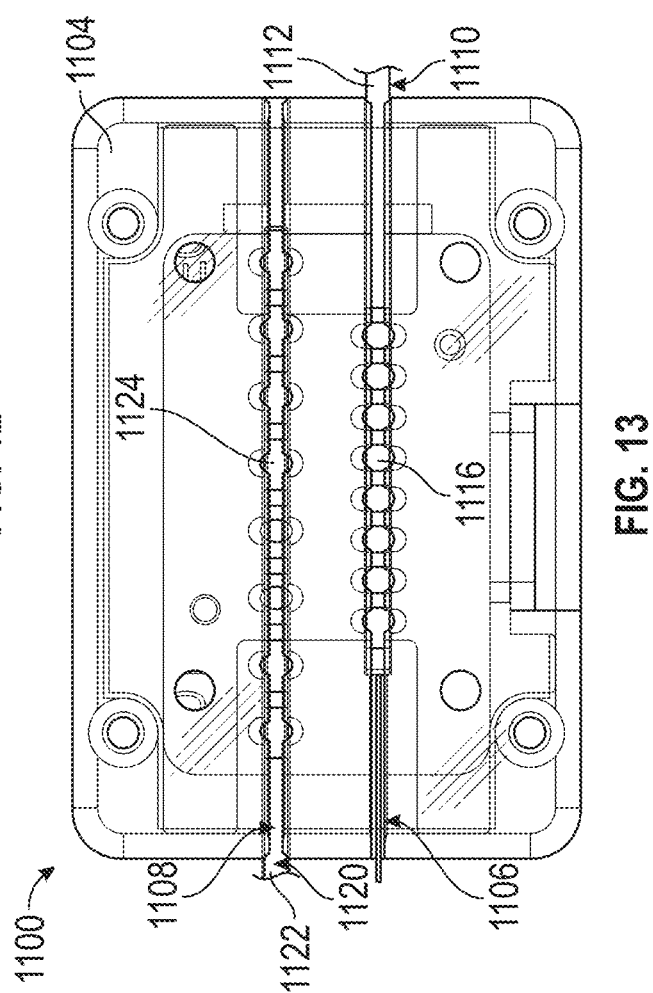

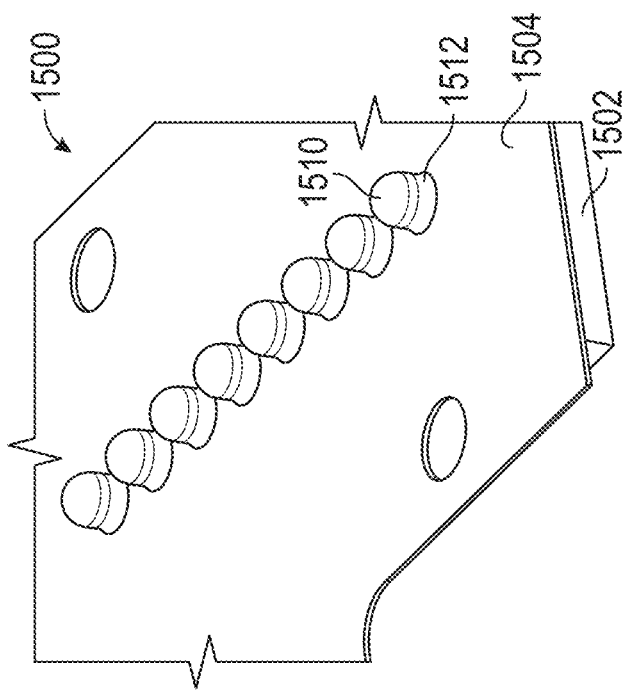
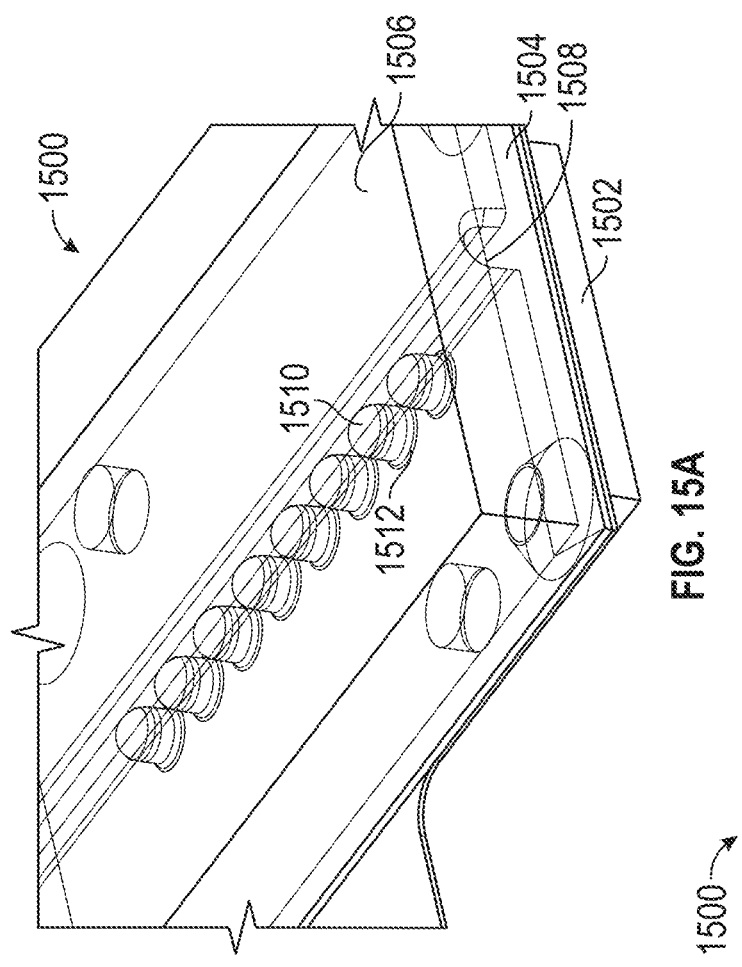
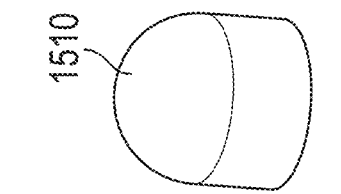
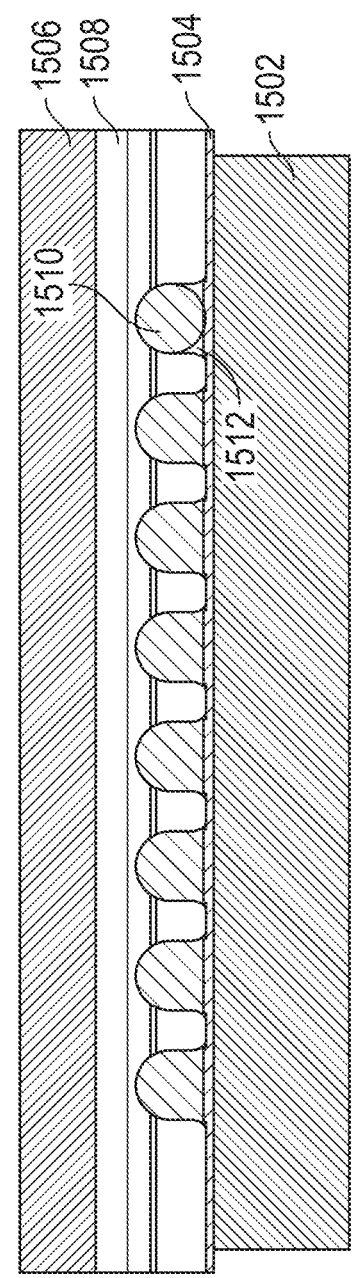
FIG. 15A
FIG. 15B
FIG. 15C
FIG. 15D

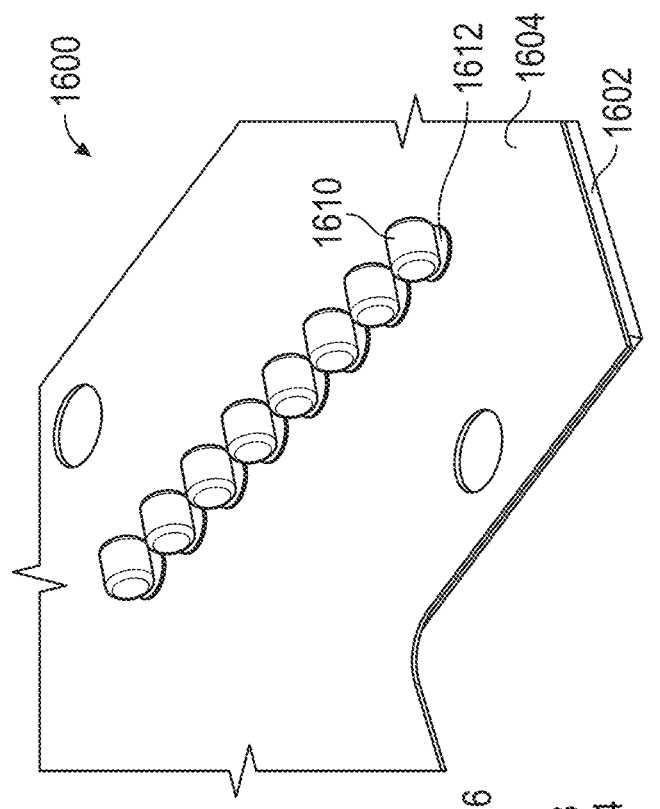
FIG. 16C
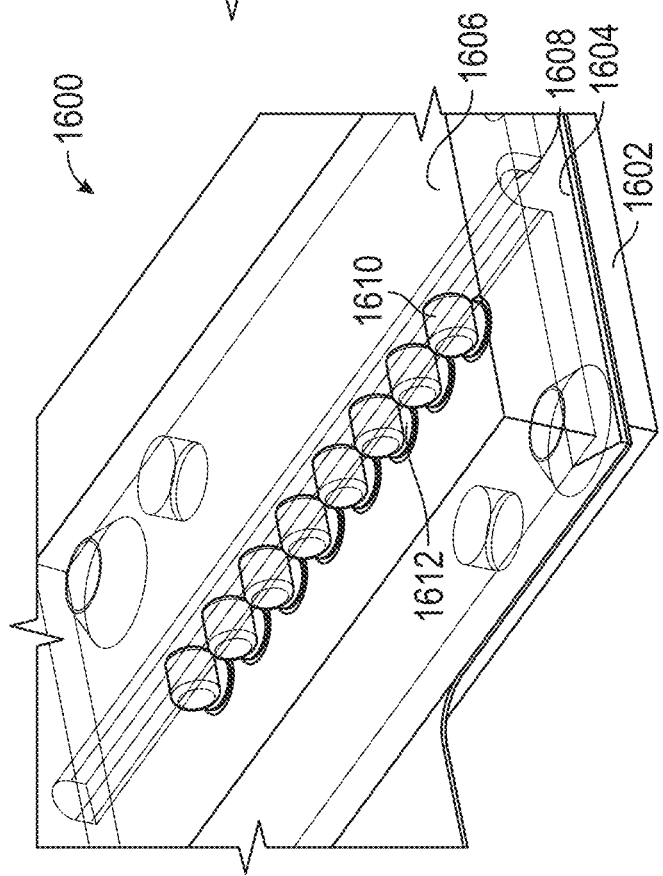
FIG. 16A
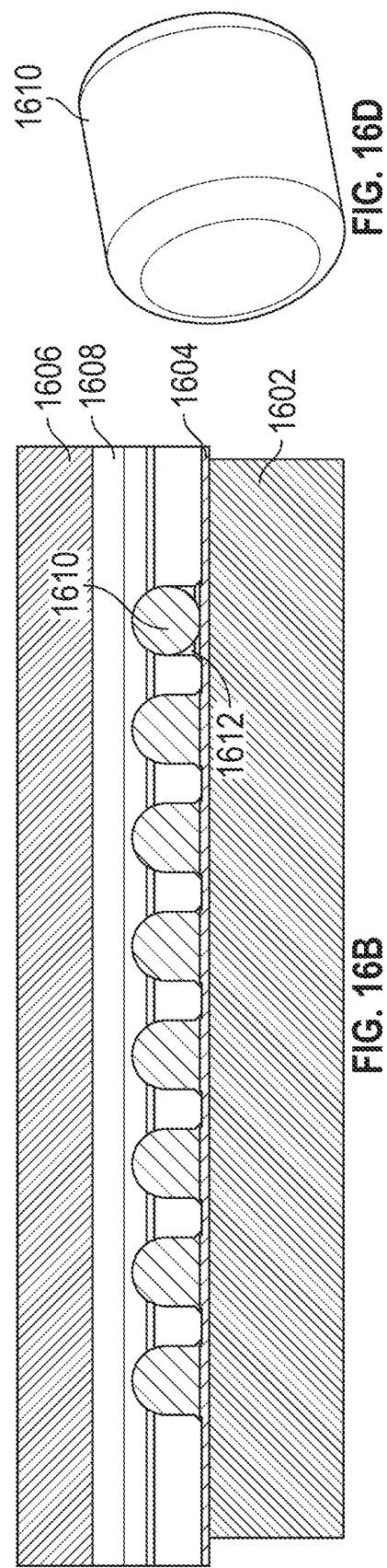
FIG. 16D
FIG. 16B

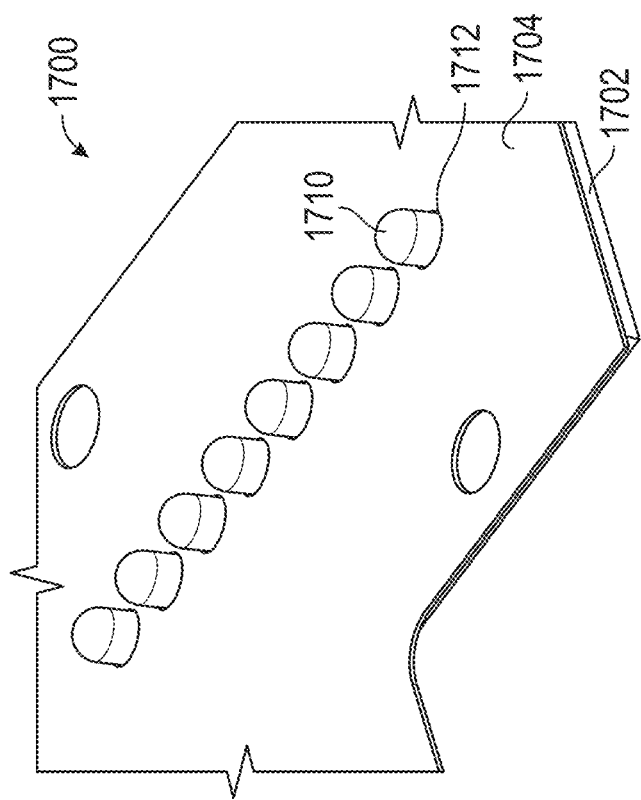
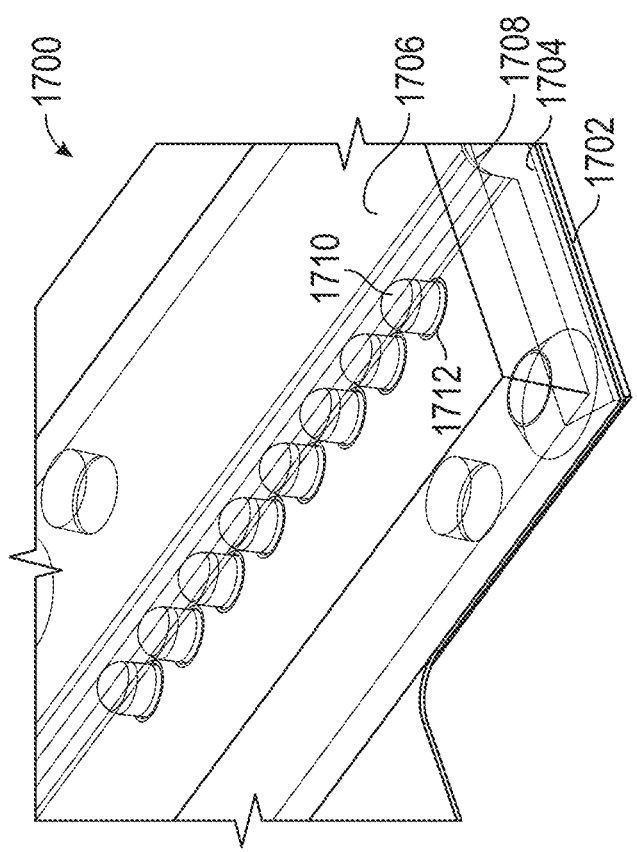
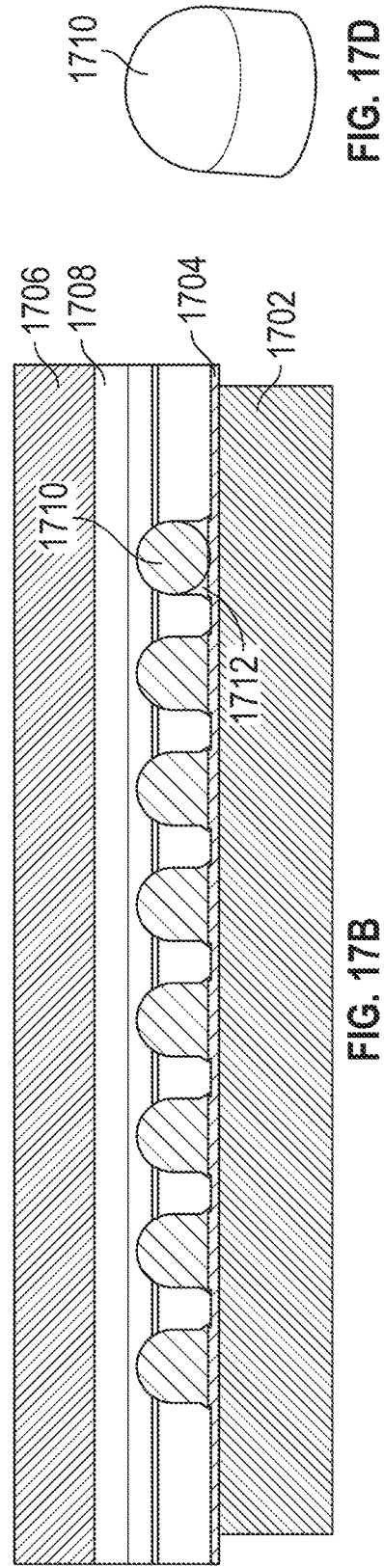
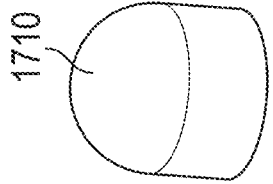
FIG. 17A
FIG. 17B
FIG. 17C
FIG. 17D

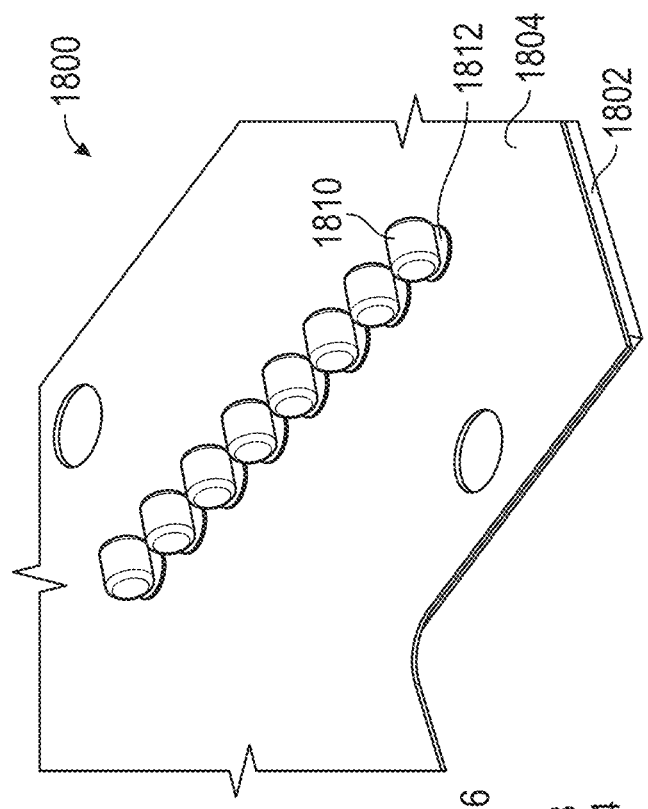
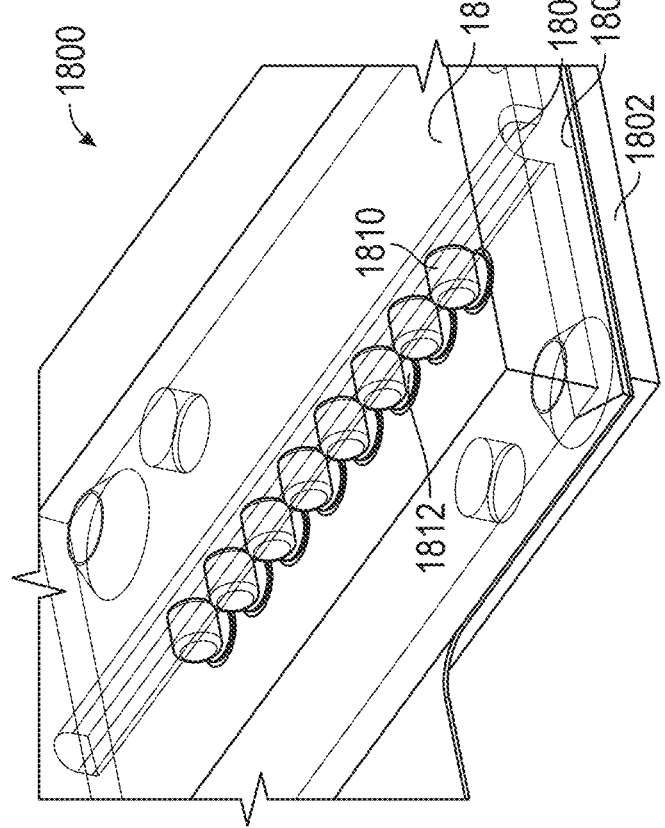
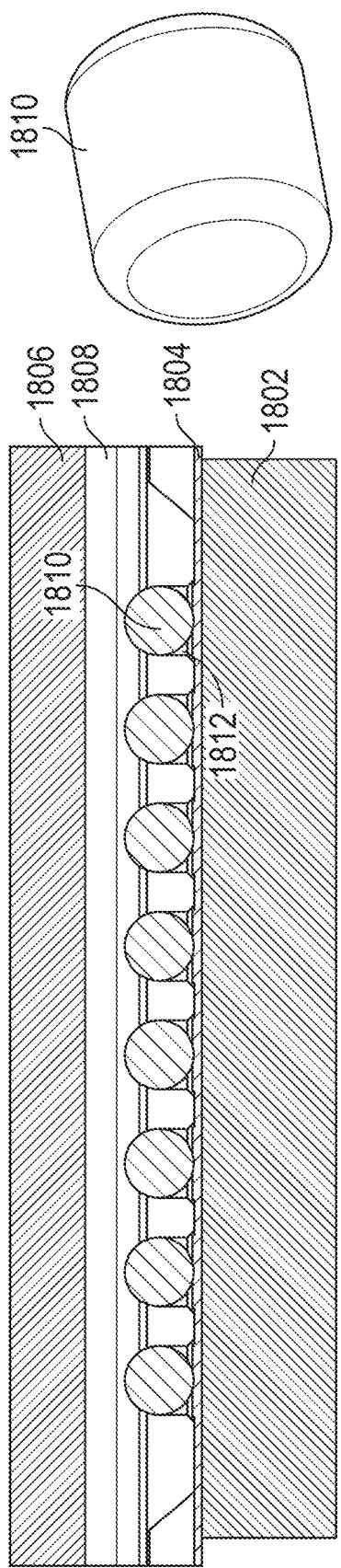
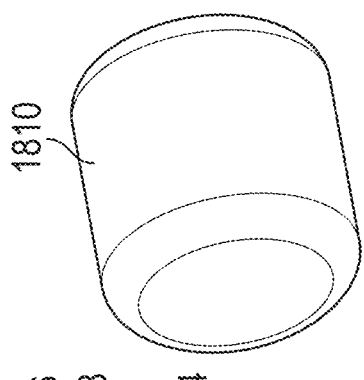
FIG. 18A
FIG. 18B
FIG. 18C
FIG. 18D

MEDICAL LEAD CONNECTORS WITH CONTACT ELECTRODES

RELATED APPLICATIONS

This application is a Continuation-in-Part and claims the benefit of U.S. patent application Ser. No. 15/980,533, filed on May 15, 2018, which is a Continuation-in-Part of U.S. patent application Ser. No. 15/640,419, filed on Jun. 30, 2017, now U.S. Pat. No. 9,972,951; issued on May 15, 2018, the contents of which is incorporated herein by reference in its entirety.

TECHNICAL FIELD

The disclosed technology relates generally to lead connectors, and more particularly, some embodiments relate to lead connectors with contact electrodes for medical use.

BACKGROUND

Electrodes used in medical devices transfer ionic current energy into electrical current, where such currents can be amplified and be applied for various medical applications. For example, the electrodes may be applied to help diagnose various diseases, monitor the human body for specific conditions, and even facilitate medical operations during complex surgeries. Indeed, such electrodes are even known to help provide medical treatment for patients with Parkinson's disease, Alzheimer's disease, sinus, body ache, epilepsy, heart conditions, and other various medical conditions.

BRIEF SUMMARY OF EMBODIMENTS

According to various embodiments of the disclosed technology, disclosed is a lead connector that may include a base member; a flexible circuit disposed on the base member and including a plurality of electrical contacts; a plurality of contact housings mounted on the flexible circuit; and a plurality of rotatable contacts mounted at least partially within the plurality of contact housings. The plurality of contact housings are positioned to allow contact between a lead inserted into the lead connector and the plurality of rotatable contacts and between the plurality of rotatable contacts and the plurality of electrical contacts of the flexible circuit. A casing including a bottom casing and a cover member. The bottom casing comprises an array of receptacles at least partially open to and aligned with the contacts. The cover member may include a slot opening configured to receive a lead stylet. When a lead is inserted into the lead connector via an opening on the cover member, the lead may push against the plurality of rotatable contacts, electrically coupling the lead to the flexible circuit via the plurality of rotatable contacts and the plurality of electrical contacts of the flexible circuit.

In embodiments, the plurality of rotatable contacts comprise one or more of a ball contact, a radius pin, and a cylindrical pin.

In further embodiments, the base member is made of material including an elastomer.

In embodiments, the base member and the flexible circuit both deflect when the plurality of rotatable contacts are pushed downward by the lead.

In embodiments, the lead includes an array of electrical contacts that align with the plurality of rotatable contacts.

In embodiments, the plurality of rotatable contacts includes two or more rows of rotatable contacts positioned below the array of receptacles within the bottom casing, such that when the lead is inserted into the lead connector via the opening on the cover member, the lead pushes against the two or more rows of rotatable contacts, electrically coupling the lead with the flexible circuit via the rotatable contacts and the plurality of electrical contacts of the flexible circuit.

In embodiments, a given electrical contact of the lead makes contact with two or more rotatable contacts simultaneously In one embodiment of the disclosed technology, a method of using a lead connector for medical purposes includes: inserting a lead into an opening of the lead connector, the lead connector including: a base member; a flexible circuit supporting electrical connections; a plurality of contact housings mounted on the flexible circuit; a plurality of rotatable contacts mounted at least partially within the plurality of contact housings, and a casing including a bottom casing and a detachable cover member to be placed on top of the bottom casing. The plurality of contact housings are positioned to allow contact between a lead inserted into the lead connector and the plurality of rotatable contacts and between the contacts and the plurality of electrical contacts of the flexible circuit. The bottom casing includes an array of receptacles at least partially open to and aligned with the contacts. The cover member comprises an opening to receive the lead. The method further includes placing the lead into the slot opening on the lead connector till the lead pushes down on the plurality of rotatable contacts. The lead has an array of electrical contacts. The method also includes aligning the lead with the plurality of rotatable contacts, such that a given electrical contact of the lead is positioned to touch a corresponding rotatable contact In various embodiments, the flexible circuit comprises a printed circuit board.

In some embodiments, the lead makes an electrical connection with the plurality of rotatable contacts when the lead is inserted through the opening of the cover member.

In embodiments, two or more rows of rotatable contacts are positioned below the array of receptacles within the bottom casing, such that when the lead is inserted into the lead connector via the opening on the cover member, the lead pushes against the two or more rows of rotatable contacts, electrically coupling the lead with the flexible circuit via the two or more rows of rotatable contacts and the plurality of electrical contacts of the flexible circuit.

In some embodiments, the given electrical contact of the lead makes contact with two or more rotatable contacts simultaneously.

In various embodiments, the method further includes attaching the lead connector to medical equipment.

According to one embodiment of the disclosed technology, disclosed is a lead connector that may include a base member; a flexible circuit disposed on the base member and comprising a plurality of electrical contacts; a casing comprising a bottom casing and a cover member; and an array of intermediary contacts mounted to locations on the flexible circuit corresponding to the array of receptacles. The bottom casing comprises an array of receptacles at least partially open to a surface of the flexible circuit and aligned with corresponding electrical contacts on the flexible circuit. The array of intermediary contacts are electrically coupled to the flexible circuit via the plurality of electrical contacts of the flexible circuit. When a lead is inserted through the lead connector via an opening on the cover member, the lead is in contact with the array of intermediary contacts, electrically coupling the lead with the flexible circuit via the array of intermediary contacts and the plurality of electrical contacts of the flexible circuit.

In embodiments, individual ones of the array of intermediary contacts comprise one or more of a ball contact, a radius pin, and a cylindrical pin.

In some embodiments, the lead comprises an array of electrical contacts that aligns with the array of intermediary contacts.

In various embodiments, the array of intermediary contacts comprises two or more rows of intermediary contacts positioned below the array of receptacles within the bottom casing, such that when the lead is inserted into the lead connector via the opening on the cover member, the lead pushes against the two or more rows of intermediary contacts, electrically coupling the lead with the flexible circuit via the two or more rows of intermediary contacts and the plurality of electrical contacts of the flexible circuit.

In some embodiments, a given electrical contact of the lead makes contact with two or more intermediary contacts simultaneously.

In one embodiment of the disclosed technology, a method of using a lead connector for medical purposes including: inserting a lead into an opening of the lead connector, the lead connector comprising: a base member; a flexible circuit disposed on the base member and comprising a plurality of electrical contacts; a casing comprising a bottom casing and a cover member; and an array of intermediary contacts mounted to locations on the flexible circuit corresponding to the array of receptacles. The bottom casing comprises an array of receptacles at least partially open to a surface of the flexible circuit and aligned with the plurality of electrical contacts on the flexible circuit. The cover member comprises an opening to receive the lead. The array of intermediary contacts are electrically coupled to the flexible circuit via the plurality of electrical contacts of the flexible circuit. The method may further include placing the lead into the opening on the lead connector till the lead pushes down on the array of intermediary contacts, wherein the lead has an array of electrical contacts and aligning the lead with the array of intermediary contacts, such that a given electrical contact of the lead is positioned to touch a corresponding intermediary contact.

In embodiments, the array of intermediary contacts are electrically coupled to the flexible circuit via the plurality of electrical contacts of the flexible circuit.

In some embodiments, the array of intermediary contacts comprises two or more rows of intermediary contacts positioned below the array of receptacles within the bottom casing, such that when the lead is inserted into the lead connector via the opening on the cover member, the lead pushes against the two or more rows of intermediary contacts, electrically coupling the lead with the flexible circuit via the array of intermediary contacts and the plurality of electrical contacts of the flexible circuit.

In various embodiments, the given electrical contact of the lead makes contact with two or more intermediary contacts of the array of intermediary contacts simultaneously.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any technology described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Some of the figures included herein illustrate various embodiments of the disclosed technology from different viewing angles. Although the accompanying descriptive text may refer to such views as "top," "front," "back," "bottom" or "side" views, such references are merely descriptive and do not imply or require that the disclosed technology be implemented or used in a particular spatial orientation unless explicitly stated otherwise.

FIG. 12 is a diagram illustrating a top view of a lead connector connecting two leads in accordance with one embodiment of the technology described herein.

FIG. 13 is a diagram illustrating a top view of a lead connector connecting two leads in accordance with one embodiment of the technology described herein.

FIG. 15A illustrates radius pins soldered to a flexible circuit, in accordance with one embodiment of the technology described herein.

FIG. 15B illustrates radius pins soldered to a flexible circuit, in accordance with one embodiment of the technology described herein.

FIG. 15C illustrates radius pins soldered to a flexible circuit, in accordance with one embodiment of the technology described herein.

FIG. 15D illustrates a radius pin, in accordance with one embodiment of the technology described herein.

FIG. 16A illustrates cylindrical pins soldered to a flexible circuit, in accordance with one embodiment of the technology described herein.

FIG. 16B illustrates cylindrical pins soldered to a flexible circuit, in accordance with one embodiment of the technology described herein.

FIG. 16C illustrates cylindrical pins soldered to a flexible circuit, in accordance with one embodiment of the technology described herein.

FIG. 16D illustrates a cylindrical pin, in accordance with one embodiment of the technology described herein.

FIG. 17A illustrates floating radius pins mounted to a flexible circuit, in accordance with one embodiment of the technology described herein.

FIG. 17B illustrates floating radius pins mounted to a flexible circuit, in accordance with one embodiment of the technology described herein.

FIG. 17C illustrates floating radius pins mounted to a flexible circuit, in accordance with one embodiment of the technology described herein.

FIG. 17D illustrates a radius pin, in accordance with one embodiment of the technology described herein.

FIG. 18A illustrates floating radius pins mounted to a flexible circuit, in accordance with one embodiment of the technology described herein.

FIG. 18B illustrates floating radius pins mounted to a flexible circuit, in accordance with one embodiment of the technology described herein.

FIG. 18C illustrates floating radius pins mounted to a flexible circuit, in accordance with one embodiment of the technology described herein.

FIG. 18D illustrates a radius pin, in accordance with one embodiment of the technology described herein.

Figure 1A:
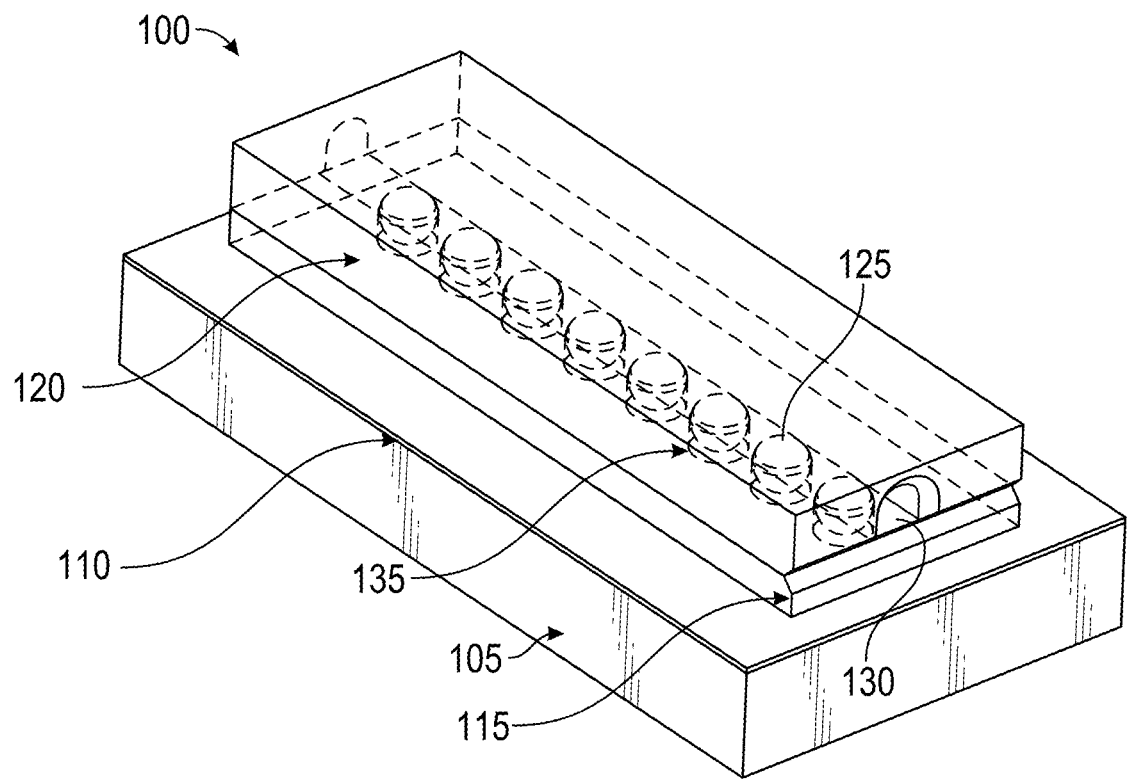
FIG. 1A is a diagram illustrating a lead connector without a lead inserted in accordance with one embodiment of the technology described herein.

The figures are not intended to be exhaustive or limiting to the precise form disclosed. It should be understood that the technology can be practiced with modification and alteration, and that the disclosed technology be limited only by the claims and the equivalents thereof.

DETAILED DESCRIPTION OF THE EMBODIMENTS

Embodiments of the technology disclosed herein are directed toward an apparatus pertaining to medical lead connectors with contact electrodes. In various embodiments, a lead wire, which may be a multi-conductor lead, includes a plurality of lead contacts disposed along the lead. The lead contacts are dimensioned and spaced apart such that when the lead is inserted into the lead connector, the lead contacts align with corresponding lead connector contacts in the lead connector housing. The lead is of a shape and diameter to be inserted in the lead connector housing, and the lead connector housing can be shaped such that it guides the lead to a position in which the lead contacts are aligned and in physical contact with the corresponding electrical contacts on the lead connector, thereby establishing an electrical connection. The connector may be configured to receive one or more leads, and the leads may include a lead stylet, a lead wire, a lead probe, a lead with cup electrodes, a lead with grabbers, a lead with snaps, or other types of leads.

The electrical contacts on the lead connector can be in the form of floating contacts that deflect to allow insertion of the lead into the lead connector housing, but that also spring back to provide good electrical contact to their corresponding lead contacts. In some embodiments, the lead connector contacts are mounted on and electrically connected to a flexible circuit board, such that the circuit board can flex to allow the lead contacts to deflect.

In embodiments, the lead connector contacts may be mounted to contact housings that allow the lead connector contacts to rotate, spin, displace, or otherwise move. For example, the contact housing may be a socket that prevents the lead connector contact from escaping and allows the lead connector contact to rotate as a lead is pushed against it. In another example, a contact housing may receive and contain a cylindrical contact, such that a lead moving against the curved surface of a cylindrical contact rolls the cylindrical contact within the contact housing. In another example, the contact housing may hold the lead connector contact in a fixed position while allowing the lead connector contact to rotate substantially freely. It should be appreciated that other contact housings and connections may be envisioned for different applications. In some embodiments, the lead connector contacts may be electrically coupled to the contact housing, which is electrically coupled and mounted to the flexible circuit board. In other embodiments, the lead connector contacts may be electrically coupled directly to the flexible circuit board.

The flexible circuit board can be mounted on an elastomeric material such as a foam or foam-like substrate to support the circuit board, allow it to flex and also provide pressure to force the lead connector contacts toward the lead contacts. The properties of the elastomeric substrate can be selected such that it provides adequate pressure to allow good electrical contact between the connector contacts and their respective lead contacts. In further embodiments, the elastomeric substrate can be selected such that it provides adequate friction to hold the lead in place in the connector body during use. In some applications, the lead connectors can be configured as disposable items that can be slid into place on the leads for use and then removed from the leads and discarded after use. An elastomeric substrate not only provides pressure for a good electrical connection, but can also allow the lead connector to flex during use, which can be an advantage in certain applications such as medical applications and other applications across various industries.

FIG. 1A is a diagram illustrating a lead connector 100 in accordance with one embodiment of the technology described herein. Additionally, FIG. 1B is a diagram illustrating a cross-sectional view of the example lead connector 100 illustrated in FIG. 1A.

Figure 1B:
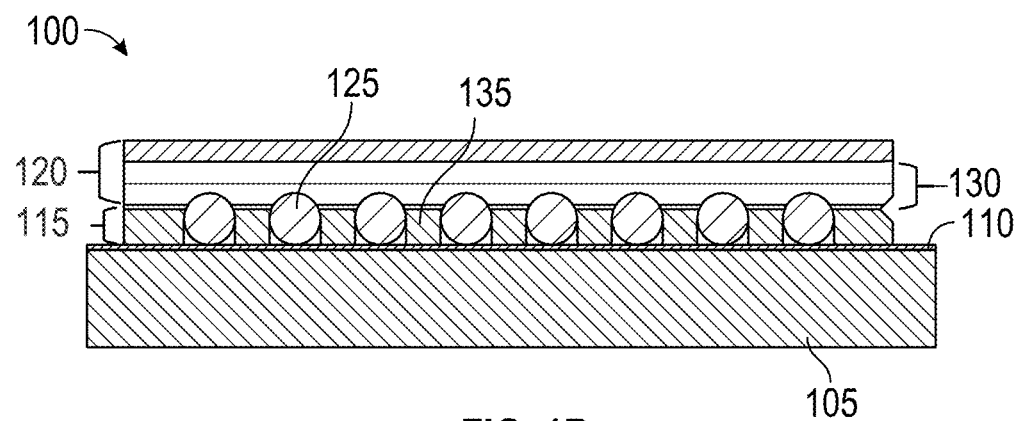
FIG. 1B is a diagram illustrating a cross-sectional view of a lead connector without a lead inserted in accordance with one embodiment of the technology described herein.

Referring now to FIGS. 1A and 1B, the example lead connector may include at least a base member 105, a flexible circuit 110, bottom casing 115, cover member 120, and lead connector contacts 125. The base member 105 may be made of an elastomeric material by way of example only. Additionally, the base member 105 may be made of any material with adequate elastic properties to allow the base member 105 to be bent, stretched, twisted, or deformed, and when released, return to its original shape and dimensions. The elastic properties of the base material may be selected to allow the base to conform to the surface to which it is applied, flex adequately to allow a lead to be inserted into opening 130 located on either or both sides of cover member 120, and spring back with adequate force to allow the lead connector contacts 125 to make adequate electrical contact with the lead contacts. However, base member 105 may be made of any material as would be appreciated by one of ordinary skill in the art.

A flexible circuit 110 may be mounted on the top surface of the base member 105. The flexible circuit 110 may include one or more layers of printed circuit connections and contacts, including traces that may be connected to or in contact with the lead connector contacts 125. As such, the flexible circuit 110 and the underlying base member 105 may support the mechanical and electrical connections needed to ensure that the proper electrical connections are made so that electronic or medical devices may be supported when connected to the lead connector 100. By way of further example, the flexible circuit 110 may be designed to flex and bend as the base member 105 flexes and bends, so that both the flexible circuit 110 and the base member 105 may experience the same or near identical movement or conformed shape.

In the illustrated example, lead connector contacts 125 are in the form of ball contacts, which may be made of or coated with a conductive material such as, for example, gold, silver, copper, graphite, platinum, tin, carbon, conductive polymers, or other conductive materials. In other embodiments, lead connector contacts 125 are in the form of solder bumps or balls or other like structures affixed to the flexible circuit 110. Lead connector contacts 125 may also be cylindrical pin contacts, radius pin contacts, or other contacts. A radius pin contact may be cylindrical on one end, and spherical, domed, or otherwise curved on the other end of the radius pin contact, as illustrated in FIGS. 15 and 17. A cylindrical pin contact may be cylindrical in a middle portion of the contact with a first diameter and taper at both ends of the contact to a second diameter, as illustrated in FIGS. 16 and 18. It should be appreciated that other lead connector contacts 125 may be envisioned for different applications and contexts.

Embodiments using ball contacts can be configured to allow the ball contacts to roll during insertion/extraction of the lead, providing easier acceptance and removal of the lead. For example, a contact housing may be mounted to flexible circuit 110. The contact housing may include or contain a contact. The contact housing may allow the lead connector contacts 125 to rotate, or move, substantially freely within the contact housing. The contact housing may be mounted to the flexible circuit by soldering the contact housing to the flexible circuit, screwing it to the flexible circuit, integrating it into the flexible circuit, gluing it onto the flexible circuit, or other mechanisms. In some embodiments, lead connector contacts 125 may be soldered, integrated, or otherwise directly coupled to flexible circuit 110.

A bottom casing 115 may be securely implanted or positioned on top of the flexible circuit 110. By way of example, the bottom casing 115 may be a structure dimensioned to hold the ball contacts in place on their corresponding contacts on flexible circuit 110. Particularly, in some embodiments, the bottom casing 115 may include individual receptacles 135 dimensioned to contain an individual electrode ball contact 125 in place and large enough to allow the ball contacts to roll within the receptacles 135. Furthermore, the bottom casing 115 may have cut-outs at the bottom of each receptacle 135 so as to expose the surface of ball contacts 125 with the top surface of their corresponding contact on flexible circuit 110. The height of the receptacles 135 can be chosen such that the top surfaces of the ball contacts extend beyond the receptacle walls. An example of this is illustrated in FIG. 1B, which shows ball contacts 125 as being taller than the walls of receptacles 135. Although not illustrated in FIG. 1B, receptacles 135 can be dimensioned with a smaller opening at the top (i.e., smaller than the diameter of the receptacle at the middle of the ball contacts) so that the receptacles 135 can hold the ball contacts in place on the contacts of flexible circuit 110.

Additionally, the bottom casing 115 may be configured so that a cover member 120 is securely fitted on top of the bottom casing 115. Furthermore, the cover member 120 may also detach from the bottom casing 115, which may allow a user or a medical professional to remove or replace the ball contacts 125 as needed.

In some configurations, the cover member 120 is dimensioned such that when there is no lead inserted in lead connector 100, there is unobstructed space directly above the ball contacts 125, as more clearly depicted in FIG. 1B. In such embodiments, when there is no lead inserted in lead connector 100 the ball contacts 125 may or may not be touching the flexible circuit 110. In embodiments, the ball contacts 125 may be soldered to the flexible circuit 110. In some embodiments, other types of contacts, such as radius pin contacts or cylindrical pin contacts may be soldered to the flexible circuit 110.

The cover member 120 may include an opening 130 on either or both ends of the cover member 120. The opening 130 may be configured to receive and guide a lead (not shown here) through the cover member 120 of the lead connector 100. Opening 130 may extend the entire length of cover member 120, or it may extend only part way through cover member 120. In some embodiments, the length of opening 130 is dimensioned such that it also forms a lead placement stop for the lead being inserted into the opening. For example, the lead placement stop (e.g., the end of the opening) may be positioned such that when the lead is inserted into the opening 130 far enough such that the lead hits the stop, the lead contacts are lined up with the lead connector contacts. In further embodiments, the lead itself can include a lead stop (such as, for example, a ring around the outer circumference of the lead) that can limit the amount by which the lead can be inserted into the lead connector housing. That is, the lead stop can be configured to contact the outer surface of cover member 120 when the lead is fully inserted.

Figure 2:
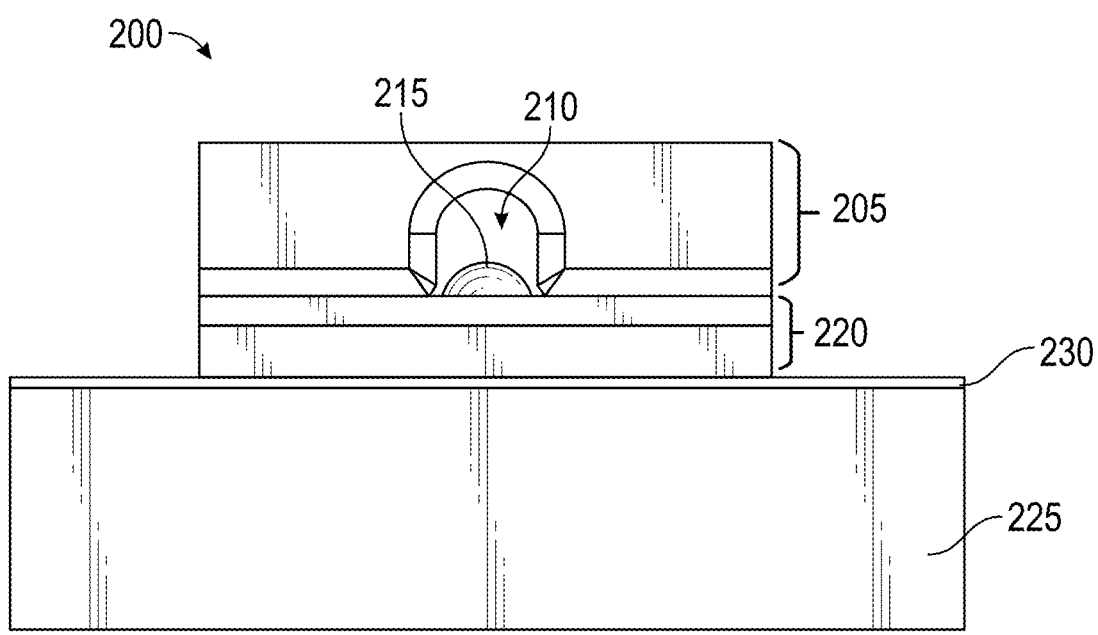
FIG. 2 is a diagram illustrating a ball contact within a lead connector in accordance with one embodiment of the technology described herein.

FIG. 2 is a diagram illustrating a side view of an example lead connector 200 in accordance with one embodiment of the technology described herein. This diagram illustrates an electrode ball contact 215 placed within a lead connector 200 as viewed through the opening. As illustrated in this example, the electrode ball contact 215 may be free to float within the bottom casing 220 and cover member 205 areas when a lead (not shown here) is not placed through the opening 210. Although the ball contacts 215 may float vertically, in some embodiments they are restrained from horizontal movement by the walls of the receptacles in bottom casing 220 (e.g., the receptacles 135 of FIG. 1). Thus, the electrode ball contact 215 may not make complete contact or be electrically engaged with the flexible circuit 230 located directly beneath the bottom casing 220. In some embodiments, the height of the opening between the top of the receptacle walls and the ceiling, or inner surface, of cover member 205 is large enough to admit a lead but small enough so that the ball contacts do not escape from their respective receptacles.

In some embodiments, electrode ball contact 215 may be housed in contact housing (not shown). As described above, the contact housing (not shown) may be mounted to flexible circuit 230 and may allow the electrode ball contact 215 to float within the contact housing (not shown), such that electrode ball contact 215 may rotate within the contact housing (not shown). In embodiments, electrode ball contact 215 may be soldered to flexible circuit 230, as described above.

Figure 3A:
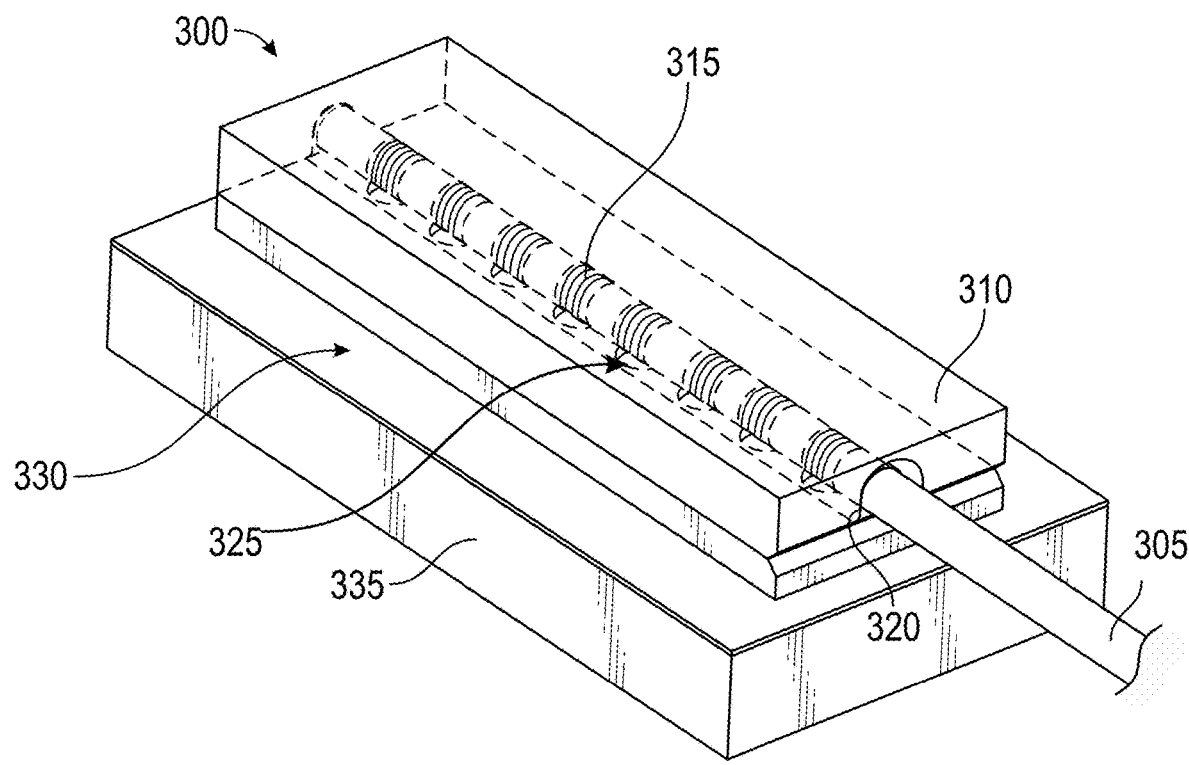
FIG. 3A is a diagram illustrating a lead connector with a lead inserted in accordance with one embodiment of the technology described herein.
Figure 3B:
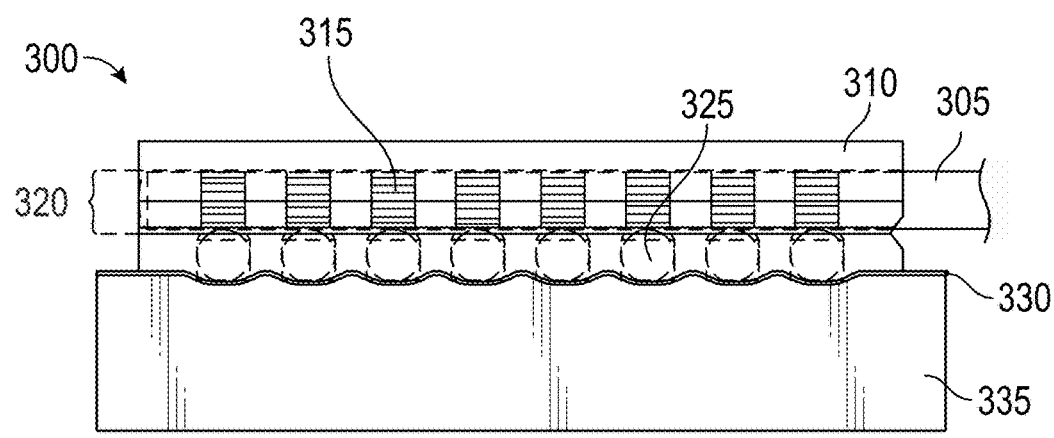
FIG. 3B is a diagram illustrating a cross-sectional view of a lead connector with a lead inserted in accordance with one embodiment of the technology described herein.

FIG. 3A is a diagram illustrating a lead connector 300 in an engaged state where a lead 305 is inserted in accordance with one embodiment of the technology described herein. FIG. 3B illustrates a side view of the lead connector 300 illustrated in FIG. 3A. An engaged state for purposes of this application may be used to indicate that a lead 305 is inserted into the lead connector 300 through the opening 320 located on both sides of the cover member 310.

Referring now to FIGS. 3A and 3B, the lead 305 may include an array of electrical contacts 315 disposed along the length of an end portion of the lead 305. In the illustrated example, there are eight electrical contacts provided as bands of conductive material that wrap completely around the lead. Each contact may be individually electrically connected to a separate internal conductor to provide, in this case, eight communication paths. Having the contacts wrap entirely around the lead allows freedom of orientation (e.g., rotational freedom) when placing the lead into the lead connector. In other embodiments, other contact configurations can be provided on the lead such as, for example, a patch contact or a band that extends only partially around the lead circumference. Although eight lead contacts 315 are illustrated, other quantities of lead contacts 315 can be provided on the lead depending on the application or the need. In some embodiments, lead contacts may be on a first end and a second end of a lead.

As this example illustrates, the electrical contacts 315 may be positioned to pass a signal between their corresponding conductors in the lead, through ball contacts 325 to the circuit board when the lead electrical contacts 315 are touching the electrical ball contacts 325. The lead 305 may be inserted within the opening 320 so that the lead electrical contacts 315 located are aligned to make contact with the ball contacts 325. When the lead 305 is inserted through the opening 320, the lead 305 may push the ball contacts 325 downward, causing them to make contact with the flexible circuit 330. This is more clearly depicted in FIG. 3B.

As illustrated, lead 305 is embodied as a lead wire, but other leads may be used, such as lead probes, lead stylets, or other leads. For example, a lead stylet may include a lead wire on a first portion of the lead stylet and a stylet on a second portion of the lead stylet. A stylet may be a malleable probe or device. A stylet may be metallic, plastic, or other malleable material. While a stylet may be configured and re-configured into different positions, once in a given position, the stylet is able to stay in the given position absent user intervention. As would be apparent to a person of ordinary skill in the art, the rigidity and malleability of the stylet may change based on a given operation. Leads may be used in various operations, such as monitoring different biological systems, confirming a value determined by another lead, providing various treatments, receiving signals, sending signals, or other uses.

As illustrated in FIG. 3B, when the lead 305 is guided and pushed through the opening 320, the lead pushes ball contacts 325 downward to engage with the flexible circuit 330. Accordingly, the diameter of the lead (and lead contacts) may be chosen to provide a desired amount of deflection of the ball contacts 325. In some embodiments, the amount of deflection of the ball contacts 325 may be adequate to flex flexible circuit 330 and compress base member 335 as shown in the illustrated example. Because the flexible circuit 330 and the base member 335 may both be made of a flexible material, and because they may have elastic properties, the flexible circuit 330 and the base member 335 may both conform to the contours of the ball contacts 325 when the lead 305 is placed through the opening 320. Resistance provided by the elastic material can provide for a better electrical contact. Also, conformance of the flexible circuit to part of the surface of ball contacts 325 (i.e., the contact on the flexible circuit 300 wrapping part way around ball contact 325) can provide a greater surface area for the electrical contact than configurations in which the flexible circuit 300 does not conform to the circumference of the ball contact 325. Additionally, by having the lead 305 push down on the ball contacts, this may further ensure that the ball contacts are properly engaged with the flexible circuit 330.

Figure 4:
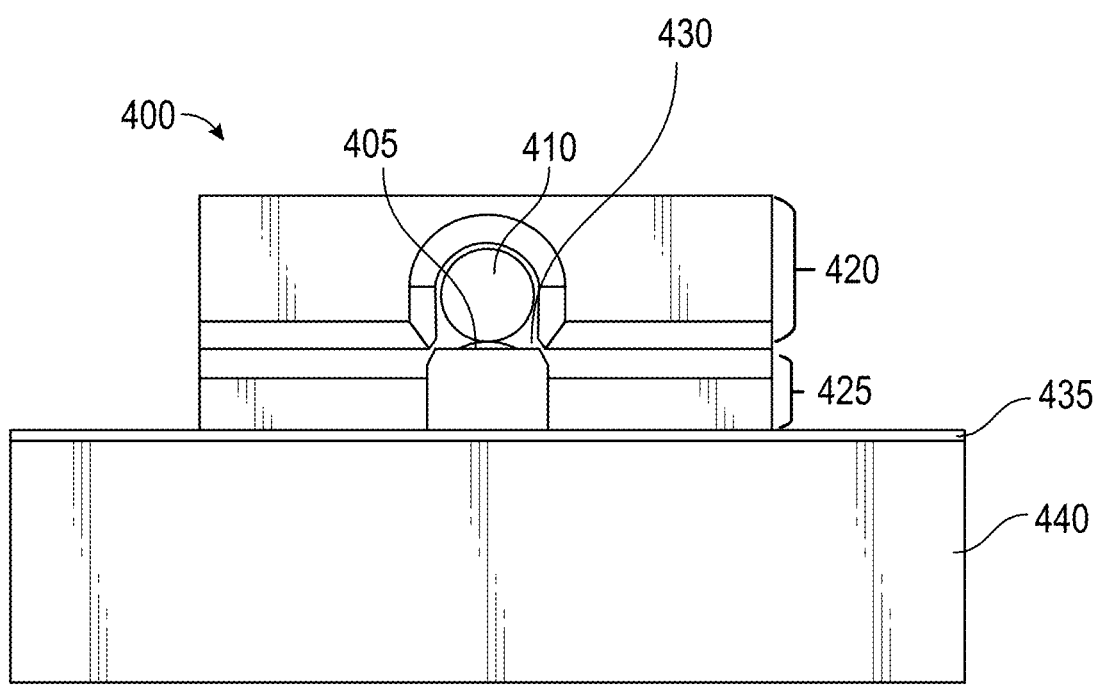
FIG. 4 is a diagram illustrating a lead connector in contact with a lead in accordance with one embodiment of the technology described.

FIG. 4 is a diagram illustrating an end view of the example lead connector where an electrode ball contact 405 is in contact with a lead 410 in accordance with one embodiment of the technology described. When comparing FIG. 2 to FIG. 4, where FIG. 2 shows a lead connector 200 without a lead, while FIG. 4 shows a lead 410 inserted within the lead connector 400 via an opening 430 on the cover member 420. As such, as the lead 410 is received through the opening 430, the diameter of the lead 410 pushes the electrode ball contact 405 downward and forces the electrode ball contact 405 to engage with the flexible circuit 435 located on top of the base member 440.

Figure 5:
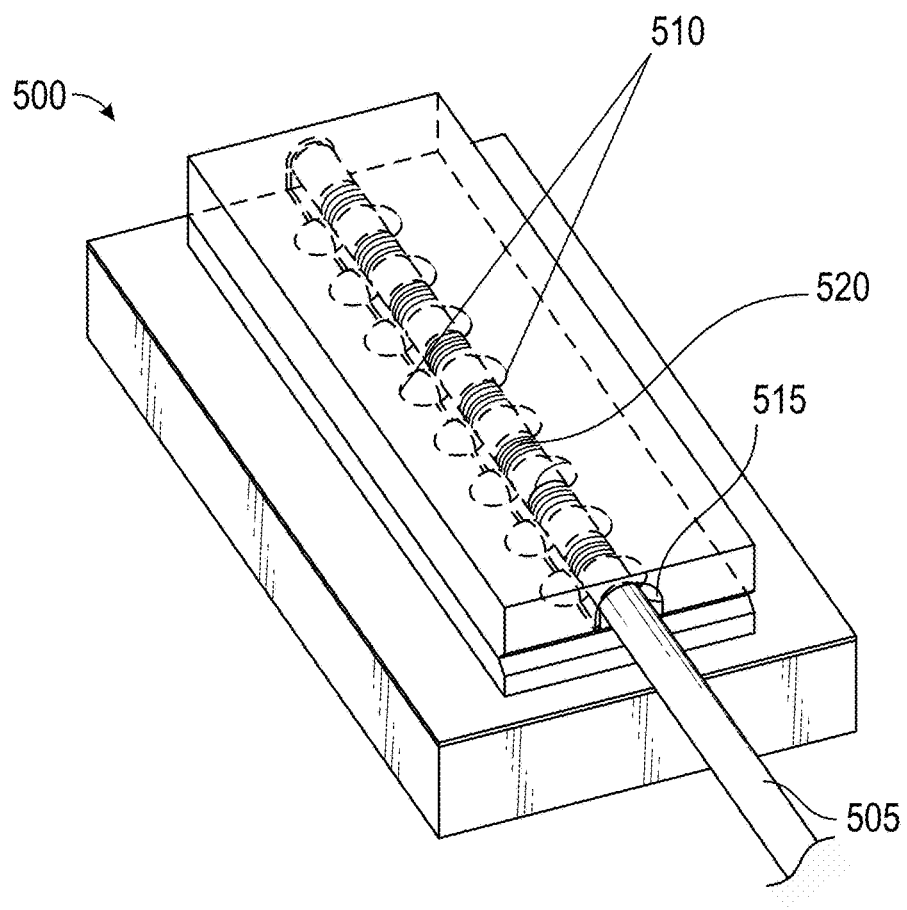
FIG. 5 is a diagram illustrating a lead connector with a lead inserted in accordance with one embodiment of the technology described herein.

FIG. 5 is a diagram illustrating another example of a lead connector 500 in an engaged state where a lead 505 is inserted in accordance with one embodiment of the technology described herein. In this embodiment, there are two rows of ball contacts 510 provided. By way of example only, the two rows of ball contacts 510 may be connected in parallel to one another so that when a lead 505 is inserted through the opening 515, a single electrical contact 520 may be simultaneously in contact with a pair of ball contacts 510 located on opposite sides of one another. In other embodiments, whether a single row or double row configuration, 2 or more ball contacts can be electrically connected to one another (e.g., via interconnects on the flexible circuit). Such embodiments provide multiple points of contact for a single electrical contact 520 of the lead 505, which may, for example, increase the current handling capacity of the connection. This is further illustrated in FIG. 6. It should be appreciated that more than two rows of ball contacts 510 may be used in different applications.

In other embodiments, each ball contact 510 in a pair may be electrically isolated from one another so that separate signal paths may be provided. In such embodiments, separate, electrically isolated lead contacts may also be provided around the lead to facilitate the channel separation.

Figure 6:
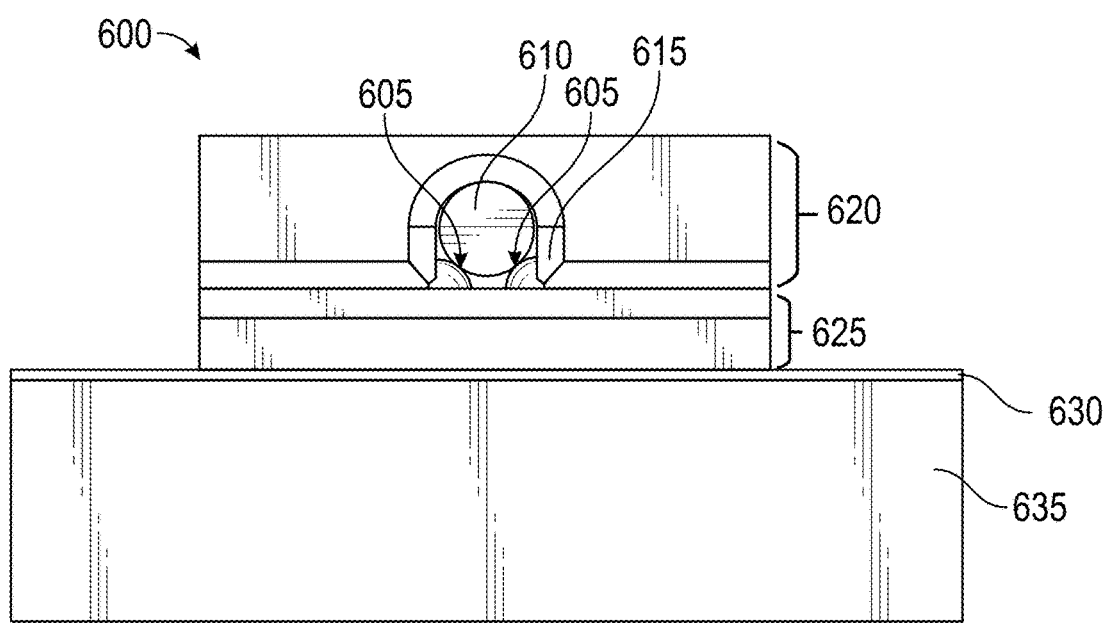
FIG. 6 is a diagram illustrating a lead connector in contact with a lead inserted in accordance with one embodiment of the technology described.

FIG. 6 is a diagram illustrating a lead connector 600 with a lead 610 in contact with multiple ball contacts 605 in accordance with one embodiment of the technology described. As illustrated, when the lead 610 is inserted through the opening 615 located on the cover member 620, the lead pushes down on the ball contacts 605. Again, with the lead 610 engaged, this may force the ball contacts 605 to make contact with the flexible circuit 630 located on top of the base member 635, and thus securing an engaged electrical connection from the electrical contacts on the lead 610 to the flexible circuit 630. Depending on the diameters of the lead and the ball contacts 605, adequate downforce may be provided to flex flexible circuit 630 and compress base member 635.

Although the base member (e.g. base member 635) is described as including an elastomeric, foam, or other like material, other base structures can be used to allow the ball contacts to deflect upon insertion of the lead yet provide force to maintain good electrical contact between the ball contacts in the lead contacts. As one example, the flexible circuit can be mounted on a metal or plastic or other plate that flexes adequately to allow the ball contacts to deflect for lead insertion, yet is adequately resistant to such flexion so that adequate electrical contact is made between the ball contacts and the electrical contacts on the lead. As another example, a backing plate can be mounted under the circuit board (or provided as a base of the circuit board) with one edge attached to a housing, such that the backing plate provides a cantilevered spring-like mechanism under the circuit board. Materials can be chosen such that the backing plate deflects adequately to allow the lead to be inserted into the connector, while providing adequate pressure on the ball contacts so that they make good electrical contact with the lead contacts.

Figure 7:
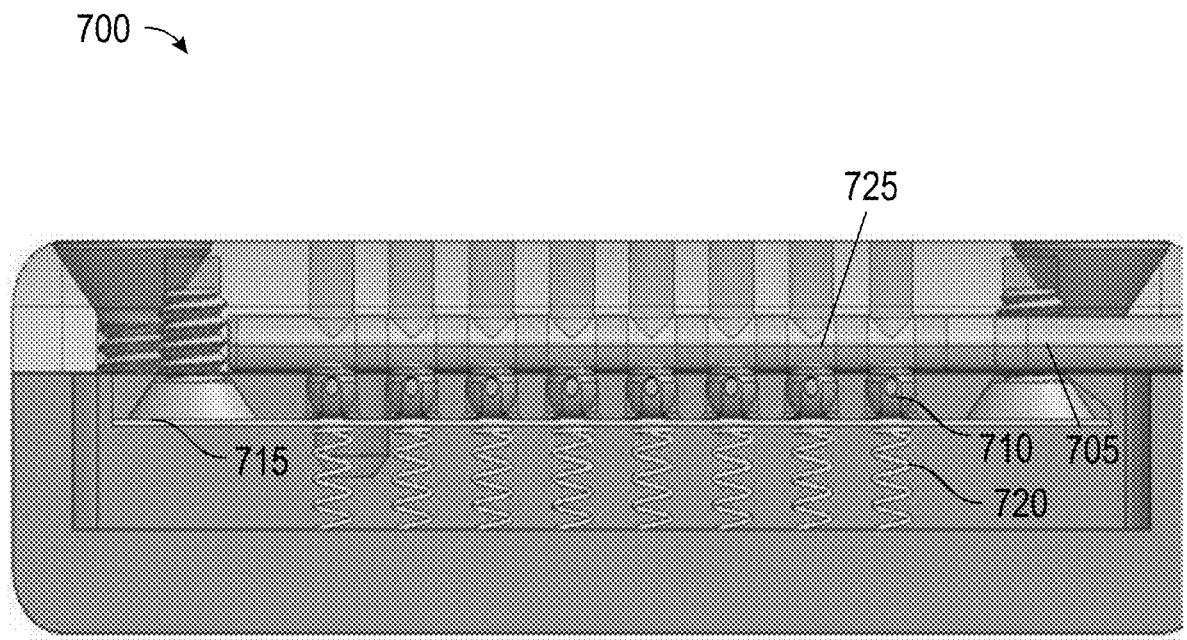
FIG. 7 is a diagram illustrating a lead connector 700 with springs below the metal ball contacts 710 in accordance with one embodiment of the technology described.

As a further example, springs can be provided beneath the circuit board to allow the ball contacts to deflect for lead insertion, yet is adequately resistant to such flexion so that adequate electrical contact is made between the ball contacts and the electrical contacts on the lead. FIG. 7 is a diagram illustrating a lead connector 700 with springs beneath the metal ball contacts 710 in accordance with one embodiment of the technology described. The springs 720 may be compression springs that are each located underneath their corresponding connector contacts 710 is illustrated in the example of FIG. 7. By way of example, the springs 720 implemented may be of various shapes and sizes, such as conical, cylindrical, hourglass, and barrel-shaped springs. The springs 720 may facilitate the electrical contact of the lead connector contacts 710 with the flexible circuit 715, and when the lead 705 is inserted through the lead connector 700, the lead 705 may push the lead connector contacts 710 downward, causing the springs 720 underneath to compress while providing adequate force in opposition to allow the lead connector contacts 710 to make adequate electrical contact with the lead contacts 725. Although the illustrated example shows one spring aligned with each contact, as another example, the circuit board may be a rigid board and one or more springs mounted to apply pressure against the circuit board, allowing the flexible circuit 715 to deflect upon lead insertion.

Figure 8:
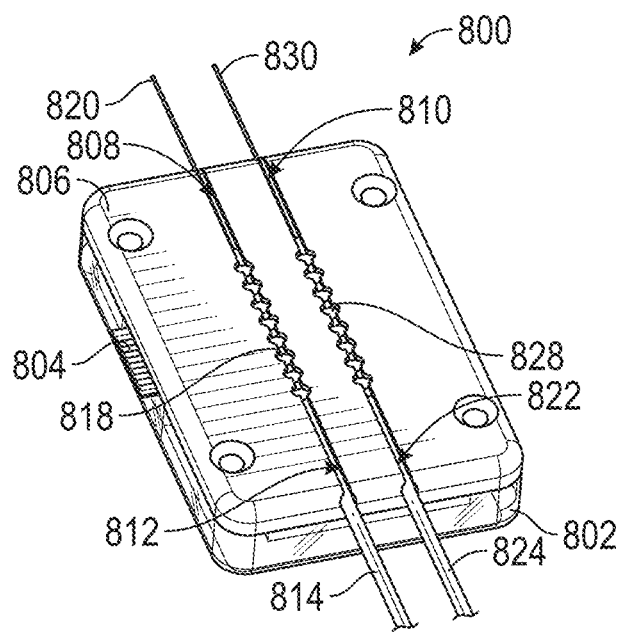
FIG. 8 is a diagram illustrating a perspective view of a lead connector with a stylet-type lead inserted in accordance with one embodiment of the technology described herein.
Figure 9:
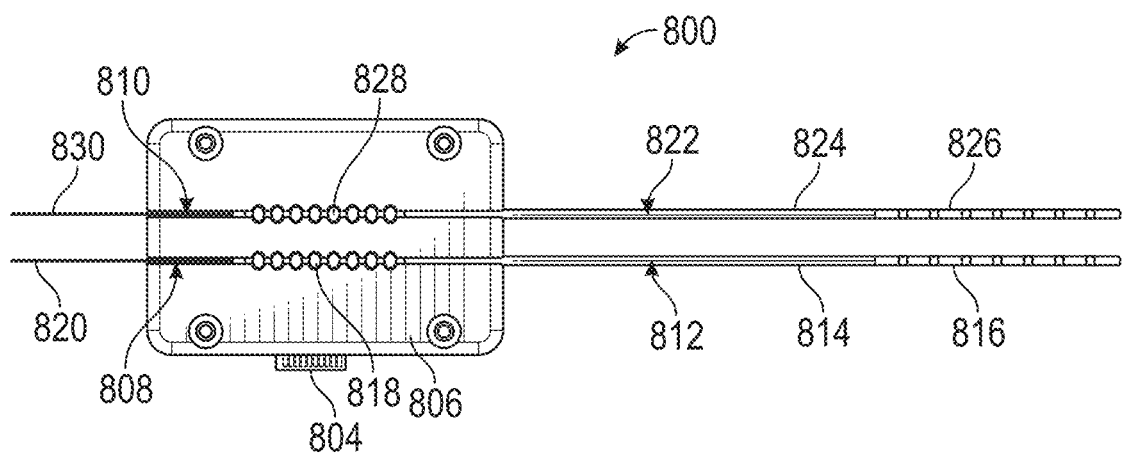
FIG. 9 is a diagram illustrating a top view of a lead connector with a stylet-type lead inserted in accordance with one embodiment of the technology described herein.
Figure 10:
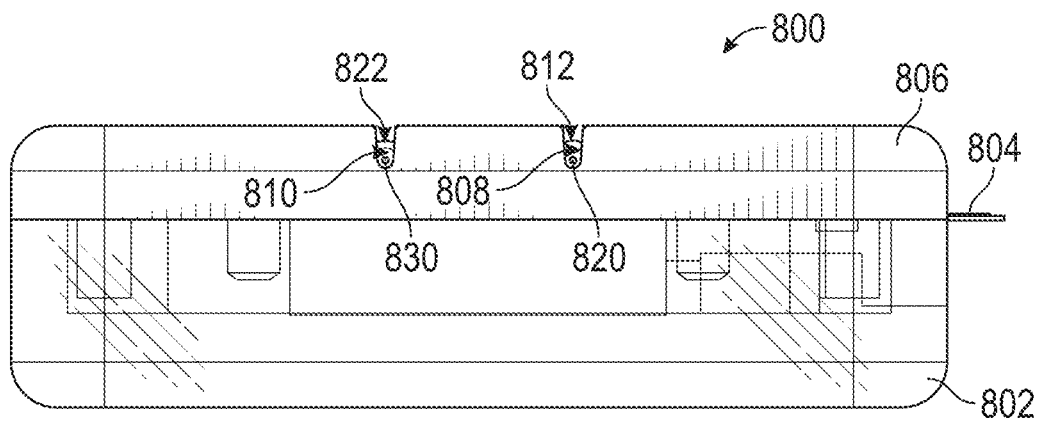
FIG. 10 is a diagram illustrating a side view of a lead connector with a stylet-type lead inserted in accordance with one embodiment of the technology described herein.

FIGS. 8, 9 and 10 are diagrams illustrating perspective, top, and side views, respectively, of lead connector 800 with lead stylets 812 and 822 inserted in accordance with embodiments of the technology described herein. Referring to FIG. 8, lead connector 800 may include base member 802, flexible circuit 804, and detachable cover member 806. Flexible circuit 804 may be disposed on base member 802. Cover member 806 may be couplable to base member 802. Cover member 806 may include slot openings 808 and 810 configured to receive lead stylets 812 and 822. Slot opening 808 may be configured to receive lead stylet 812. Slot openings 808 and 810 may be substantially parallel to each other. Slot opening 808 may keep lead stylet 812 inserted via a press fit in slot opening 808. Slot opening 808 may be flexible, such that a top portion of slot opening 808 may be configured to spread apart as lead stylet 812 is inserted into cover member 806. The top portion of slot opening 808 may be configured to cover a portion of the top of lead stylet 812 when lead stylet 812 is inserted. A person of ordinary skill in the art will recognize that other mechanisms may be used to keep lead stylet 812 inserted into cover member 806.

As illustrated, slot opening 808 may be configured to receive a proximal end of lead stylet 812 and allow for clearance of stylet portion 818 of lead stylet 812. When lead stylet 812 is inserted, stylet portion 820 may begin within the edges of lead connector 800. When lead stylet 812 is properly inserted, stylet portion 820 of lead stylet 812 may extend beyond the edge of lead connector 800. The proximal end of lead stylet 812 may be stylet portion 820 of lead stylet 812.

The distal end of lead stylet 812 may include lead wire portion 814 of lead stylet 812. Lead wire portion 814 may include the remaining portion of lead stylet 812. In some embodiments, a length of lead wire portion 814 may range from about half the length of stylet portion 820 to about five times the length of stylet portion 820. As illustrated, the length of lead wire portion 814 may be about three times the length of stylet portion 820. Lead wire portion 814 may be adjacent to stylet portion 818. In some embodiments, slot opening 808 may also receive part of lead wire portion 814.

Referring to FIG. 9, lead wire portion 814 may include lead contacts 816 and 818. As illustrated, lead contacts 818 may be adjacent to stylet portion 820, and lead contacts 816 may be on an opposite end of lead contacts 818 on lead wire portion 814. When lead stylet 812 is inserted into lead connector 800 via slot opening 808, lead stylet 812 may be electrically coupled to flexible circuit 804 via lead contacts 816 or lead contacts 818. For example, as illustrated, lead contacts 816 are pressed against ball contacts (not shown), which, in turn, are pressed downward against flexible circuit 804. In some embodiments, when lead stylets 812 and 822 are inserted, such that lead contacts 818 and 828, respectively, are in contact with corresponding ball contacts (not shown), lead stylets 812 and 822 may be electrically coupled to each other via a flexible circuit, as is described in further detail in FIGS. 11-13. In embodiments, when lead stylets 812 and 822 are inserted, such that lead contacts 818 and 828, respectively, are in contact with corresponding ball contacts (not shown), lead stylets 812 and 822 may send and receive separate signals.

As previously described, lead contacts 816 and 820 may be provided as bands of conductive material that extend partially or completely around lead stylets 812 and 822. In addition, as previously described, lead stylets 812 and 822 may secure an engaged electrical connection to flexible circuit 804 via the ball contacts (not shown) and lead contacts 818 and 828, respectively. Similarly, as previously described, lead stylets 812 and 822 may be able to flex flexible circuit 804 and compress base member 802. Lead stylet 822 may be substantially similar to lead stylet 812.

A portion of flexible circuit 804 may be external to lead connector 800, such that flexible circuit 804 can be coupled to an electronic device (not shown). When lead stylets 812 and 822 are engaged with flexible circuit 804 via the ball contacts (not shown), the external portion of flexible circuit 804 may help connect lead stylets 812 and 822 to electronic devices (not shown). As will be understood by a person having ordinary skill in the art, multiple leads may be incorporated into lead connector 800.

Figure 11:
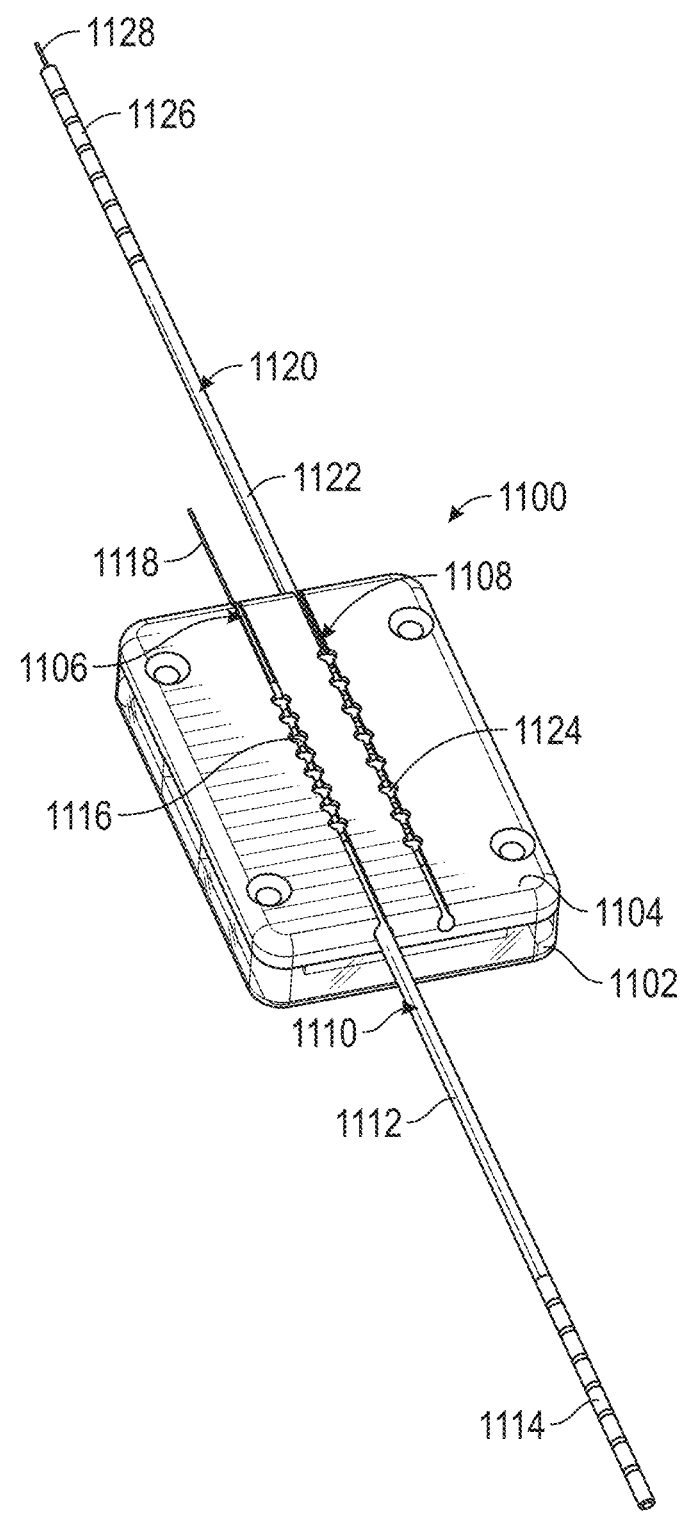
FIG. 11 is a diagram illustrating a perspective view of a lead connector connecting two leads in accordance with one embodiment of the technology described herein.

FIGS. 11, 12 and 13 are diagrams illustrating perspective and top views, respectively, of a lead connector 1100 electrically coupling leads 1110 and 1120, in accordance with one embodiment of the technology described herein. Referring to FIG. 11, lead connector 1100 may include base member 1102, flexible circuit (not shown), and detachable cover member 1104. Lead connector 1100 may electrically couple leads 1110 and 1120 together. Leads 1110 and 1120 may be illustrated as lead stylets, but other combinations of leads can be used, such as a lead wire with a lead stylet, two lead wires, a lead wire with a lead probe, a lead stylet with a lead probe, two lead probes, or other combinations of leads.

Cover member 1104 may include slot openings 1106 and 1108. Slot openings 1106 and 1108 may be substantially parallel to each other. Stylet portion 1118 of lead 1110 may be placed in slot opening 1106 such that lead contacts 1116 are in contact with a corresponding array of ball contacts (not shown), and lead wire portion 1122 of lead 1120 may be placed in slot opening 1108 such that lead contacts 1124 are in contact with a corresponding array of ball contacts (not shown). Lead connector 1100 may electrically couple leads 1110 and 1120 via the arrays of ball contacts (not shown) and the flexible circuit (not shown). For example, when lead 1110 is inserted into the lead connector 1100 via the slot opening 1106, lead 1110 may be electrically coupled to the flexible circuit (not shown) via a first array of ball contacts (not shown). The flexible circuit (not shown) may have a plurality of electrical contacts corresponding to the positions of the arrays of ball contacts (not shown). When leads 1110 and 1120 are inserted into the lead connector such that lead contacts 1116 and 1124 are in contact with corresponding arrays of ball contacts, the first array of ball contacts (not shown) may be coupled to the second array of ball contacts (not shown) via the electrical contacts of the flexible circuit (not shown). When lead 1120 is inserted into lead connector 1100 such that lead contacts 1124 are in contact with a corresponding array of ball contacts (not shown), the flexible circuit (not shown) may be electrically coupled to lead 1120 via the second array of ball contacts (not shown). Therefore, lead 1110 may be electrically coupled to lead 1120.

The length of lead 1110 may be extended when contacts 1116 and 1124 are inserted, placed, coupled, or otherwise connected to lead connector 1100. For example, a signal received by lead 1120 may be processed through lead connector to 1110, and vice versa. As illustrated, two lead wires are connected to the lead connector, however, as will be understood by a person having ordinary skill in the art, more than two leads may be incorporated into lead connector 1100. As previously described, lead contacts 1114, 1116, 1124, and 1126 may be provided as bands of conductive material, and leads 1110 and 1120 may flex flexible circuit (not shown) and compress base member 1102.

Figure 14C:
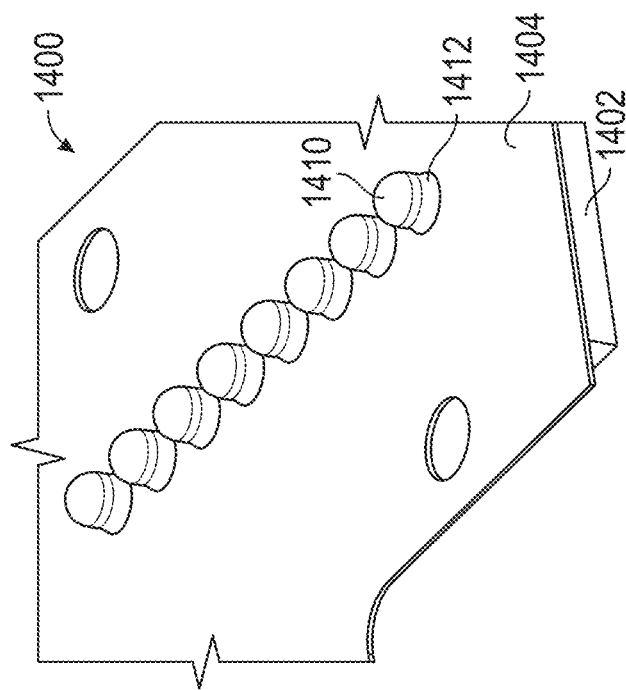
FIG. 14C illustrates a ball contact soldered to a flexible circuit, in accordance with one embodiment of the technology described herein.
Figure 14A:
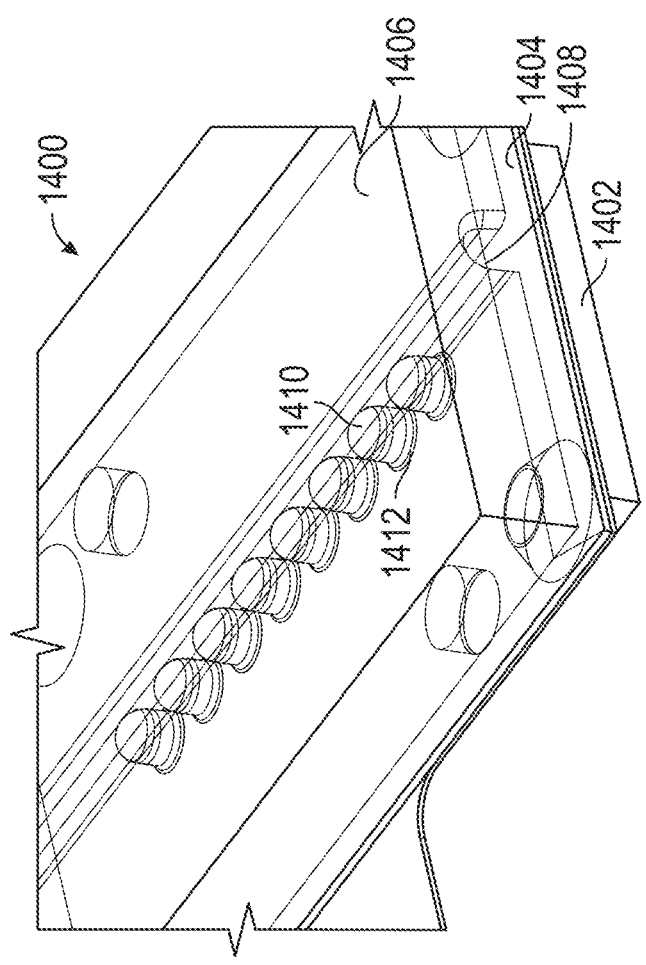
FIG. 14A illustrates ball contacts soldered to a flexible circuit, in accordance with one embodiment of the technology described herein.
Figure 14B:
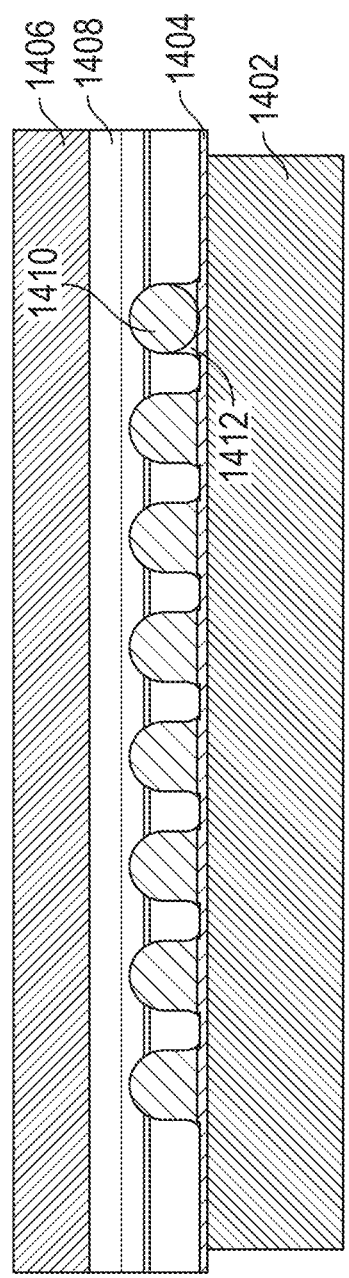
FIG. 14B illustrates ball contacts soldered to a flexible circuit, in accordance with one embodiment of the technology described herein.

FIGS. 14A, 14B and 14C illustrate ball contacts soldered to a flexible circuit, in accordance with one embodiment of the technology described herein. Referring to FIG. 14A, lead connector 1400 may include base member 1402, flexible circuit 1404, and detachable cover member 1406. Detachable cover member 1406 may include opening 1408. Ball contact 1410 may be soldered to flexible circuit 1404 with solder 1412. As described above, base member 1402 may be made of an elastomeric material, foams, or other materials. Lead connector 1400 may electrically couple a lead (not shown) to flexible circuit 1404 via the ball contacts 1410. As described above, flexible circuit 1404 may have a plurality of electrical contacts, or traces, corresponding to the positions of ball contacts 1410. FIG. 14B illustrates a side view of the example illustrated in FIG. 14A. FIG. 14C illustrates lead connector 1400 without detachable cover member 1406.

FIGS. 15A, 15B, 15C and 15D illustrate radius pins soldered to a flexible circuit, in accordance with one embodiment of the technology described herein. Referring to FIG. 15A, lead connector 1500 may include base member 1502, flexible circuit 1504, and detachable cover member 1506. Detachable cover member 1506 may include opening 1508. Radius pin 1510 may be soldered to flexible circuit 1504 with solder 1512. As described above, base member 1502 may be made of an elastomeric material, foams, or other materials. Lead connector 1500 may electrically couple a lead (not shown) to flexible circuit 1504 via the radius pins 1510. As described above, flexible circuit 1504 may have a plurality of electrical contacts, or traces, corresponding to the positions of radius pins 1510. FIG. 15B illustrates a side view of the example illustrated in FIG. 15A. FIG. 15C illustrates lead connector 1500 without detachable cover member 1506. FIG. 15D illustrates radius pin 1510, in accordance with one embodiment of the present disclosure.

FIGS. 16A, 16B, 16C and 16D illustrate cylindrical pins soldered to a flexible circuit, in accordance with one embodiment of the technology described herein. Referring to FIG. 16A, lead connector 1600 may include base member 1602, flexible circuit 1604, and detachable cover member 1606. Detachable cover member 1606 may include opening 1608. Cylindrical pin 1610 may be soldered to flexible circuit 1604 with solder 1612. As described above, base member may be made of an elastomeric material, foams, or other materials. Lead connector 1600 may electrically couple a lead (not shown) to flexible circuit 1604 via cylindrical pins 1610. As described above, flexible circuit 1604 may have a plurality of electrical contacts, or traces, corresponding to the positions of the cylindrical pins 1610. FIG. 16B illustrates a side view of the example illustrated in FIG. 16A. FIG. 16C illustrates lead connector 1600 without detachable cover member 1606. FIG. 16D illustrates radius pin 1610, in accordance with one embodiment of the present disclosure.

FIGS. 17A, 17B, 17C and 17D illustrate floating radius pins mounted to a flexible circuit, in accordance with one embodiment of the technology described herein. Referring to FIG. 17A, lead connector 1700 may include base member 1702, flexible circuit 1704, and detachable cover member 1706. Detachable cover member 1706 may include opening 1708. Contact housings 1712 may be mounted to flexible circuit 1704. Contact housing 1712 may be mounted to flexible circuit 1704 by soldering contact housing 1712, integrating contact housing 1712 into flexible circuit 1704, or otherwise mounting contact housing 1712 to flexible circuit 1704. Radius pin 1710 may be coupled to contact housing 1712. Radius pin 1710 may be able to rotate, spin, shift, and/or otherwise move within contact housing 1712. It should be appreciated that other contact housings may be used, such as, for example, a contact housing that envelopes radius pin 1710 and is partially open on a top to contact a lead and partially open on a bottom to contact the flexible circuit. As described above, base member 1702 may be made of an elastomeric material, foams, or other materials. Lead connector 1700 may electrically couple a lead (not shown) to flexible circuit 1704 via radius pins 1710. As described above, flexible circuit 1704 may have a plurality of electrical contacts, or traces, corresponding to the positions of radius pins 1710. FIG. 17B illustrates a side view of the example illustrated in FIG. 17A. FIG. 17C illustrates lead connector 1700 without detachable cover member 1706. FIG. 17D illustrates cylindrical pin 1710, in accordance with one embodiment of the present disclosure.

FIGS. 18A, 18B, 18C and 18D illustrate floating cylindrical pins mounted to a flexible circuit, in accordance with one embodiment of the technology described herein. Referring to FIG. 18A, lead connector 1800 may include base member 1802, flexible circuit 1804, and detachable cover member 1806. Detachable cover member 1806 may include opening 1808. Contact housings 1812 may be mounted to flexible circuit 1804. Contact housing 1812 may be mounted to flexible circuit 1804 by soldering contact housing 1812 onto flexible circuit 1804, integrating contact housing 1812 into flexible circuit 1804, or otherwise mounting contact housing 1812 to flexible circuit 1804. Cylindrical pin 1810 may be coupled to contact housing 1812. Cylindrical pin 1810 may be able to rotate, spin, shift, and/or otherwise move within contact housing 1812. It should be appreciated that other contact housings may be used, such as, for example, a contact housing that envelopes cylindrical pin 1810 and is partially open on a top to contact a lead and partially open on a bottom to contact the flexible circuit. As described above, base member 1802 may be made of an elastomeric material, foams, or other materials. Lead connector 1800 may electrically couple a lead (not shown) to flexible circuit 1804 via cylindrical pins 1810. As described above, flexible circuit 1804 may have a plurality of electrical contacts, or traces, corresponding to the positions of cylindrical pins 1810. FIG. 18B illustrates a side view of the example illustrated in FIG. 18A. FIG. 18C illustrates lead connector 1800 without detachable cover member 1806. FIG. 18D illustrates cylindrical pin 1810, in accordance with one embodiment of the present disclosure.

Figure 19B:
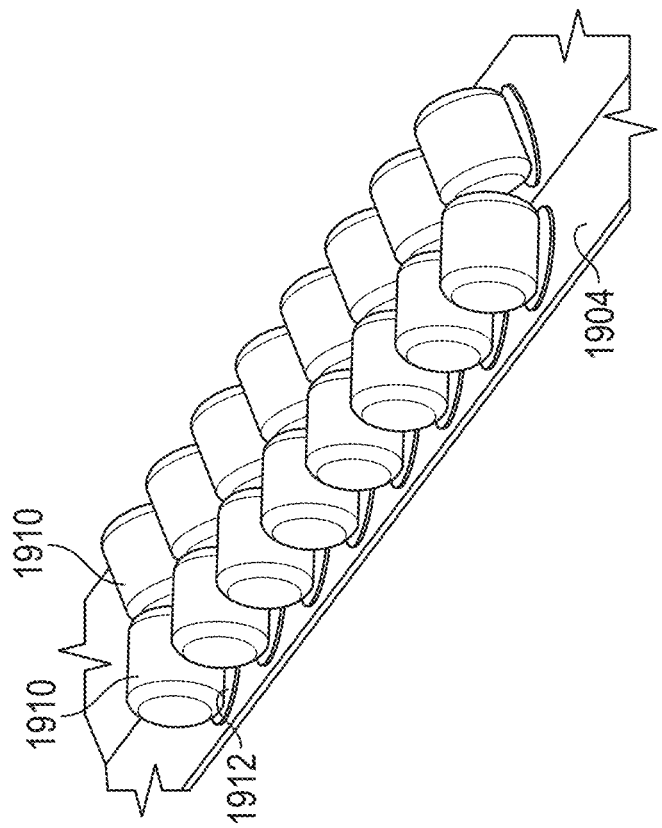
FIG. 19B illustrates double rows of pin contacts, in accordance with one embodiment of the technology described herein.
Figure 19C:
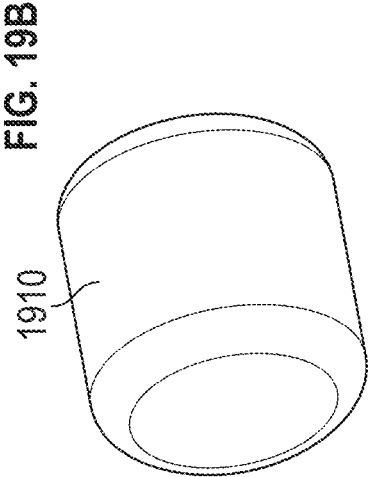
FIG. 19C illustrates a cylindrical pin, in accordance with one embodiment of the technology described herein.
Figure 19A:
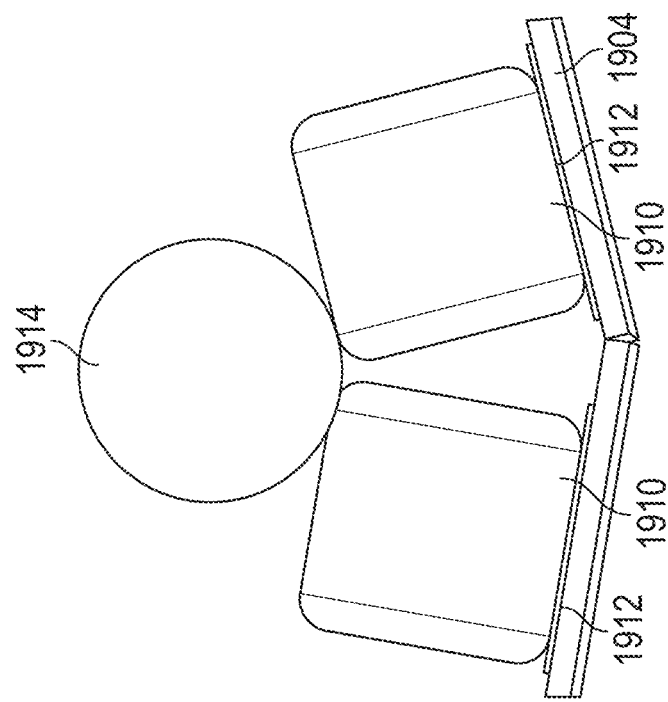
FIG. 19A illustrates double rows of pin contacts with a lead, in accordance with one embodiment of the technology described herein.

FIGS. 19A, 19B and 19C illustrate double rows of pin contacts, in accordance with one embodiment of the technology described herein. Referring to FIG. 19A, flexible circuit 1904 may include two portions, such that the two rows of cylindrical pins 1910 can be angled toward each other, forming a "V-like" shape. In some embodiments, the base member (not shown) may be re-shaped and re-sized to position the two rows of cylindrical pins 1910 such that they are angled toward each other. When lead 1914 is inserted into the lead connector, the two rows of cylindrical pins 1910 may simultaneously contact lead 1914. The two rows of cylindrical pins 1910 may be soldered to flexible circuit 1904 using solder, such as described above, or contact housings 1912 may be mounted to the flexible circuit, such as described above 1910. Additional contact with lead 1914 via cylindrical pins 1910 may provide a better connection for lead 1914 to flexible circuit 1904. As described above, flexible circuit 1904 may have a plurality of electrical contacts, or traces, corresponding to the positions of cylindrical pins 1910. It should be appreciated that more than two rows of cylindrical pins 1910 may be used, such as for example, a third row of cylindrical pins 1910 directly underneath lead 1914. FIG. 19B illustrates a perspective view of flexible circuit 1904 and the two rows of cylindrical pins 1910. FIG. 19C illustrates cylindrical pin 1510, in accordance with one embodiment of the present disclosure.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A lead connector comprising:
a base member;
a flexible circuit disposed on the base member and comprising a plurality of electrical contacts;
a plurality of contact housings mounted on the flexible circuit;
a plurality of rotatable contacts mounted at least partially within the plurality of contact housings, wherein the plurality of contact housings are positioned to allow contact between a lead inserted into the lead connector and the plurality of rotatable contacts and between the plurality of rotatable contacts and the plurality of electrical contacts of the flexible circuit; and
a casing comprising a bottom casing and a cover member, wherein the bottom casing comprises an array of receptacles at least partially open to and aligned with the plurality of electrical contacts;
wherein when a lead is inserted into the lead connector via an opening on the cover member, the lead pushes against the plurality of rotatable contacts, electrically coupling the lead to the flexible circuit via the plurality of rotatable contacts and the plurality of electrical contacts of the flexible circuit.

2. The lead connector of claim 1, wherein the plurality of rotatable contacts comprise one or more of a ball contact, a radius pin, and a cylindrical pin.

3. The lead connector of claim 1, wherein the base member is made of material comprising an elastomer.

4. The lead connector of claim 1, wherein the base member and the flexible circuit both deflect when the plurality of rotatable contacts are pushed downward by the lead.

5. The lead connector of claim 1, wherein the lead comprises an array of electrical contacts that align with the plurality of rotatable contacts.

6. The lead connector of claim 1, wherein the plurality of rotatable contacts comprises two or more rows of rotatable contacts positioned below the array of receptacles within the bottom casing, such that when the lead is inserted into the lead connector via the opening on the cover member, the lead pushes against the two or more rows of rotatable contacts, electrically coupling the lead with the flexible circuit via the rotatable contacts and the plurality of electrical contacts of the flexible circuit.

7. The lead connector of claim 6, wherein a given electrical contact of the lead makes contact with two or more rotatable contacts simultaneously.

8. A method of using a lead connector for medical purposes comprising:
inserting a lead into an opening of the lead connector, the lead connector comprising:
a base member;
a flexible circuit supporting electrical connections;
a plurality of contact housings mounted on the flexible circuit;
a plurality of rotatable contacts mounted at least partially within the plurality of contact housings, wherein the plurality of contact housings are positioned to allow contact between a lead inserted into the lead connector and the plurality of rotatable contacts and between the contacts and the plurality of electrical contacts of the flexible circuit; and
a casing comprising a bottom casing and a detachable cover member to be placed on top of the bottom casing, wherein the bottom casing comprises an array of receptacles at least partially open to and aligned with the plurality of electrical contacts, and wherein the cover member comprises an opening to receive the lead;
placing the lead into the opening on the lead connector till the lead pushes down on the plurality of rotatable contacts, wherein the lead has an array of electrical contacts; and
aligning the lead with the plurality of rotatable contacts, such that a given electrical contact of the lead is positioned to touch a corresponding rotatable contact.

9. The method of claim 8, wherein the flexible circuit comprises a printed circuit board.

10. The method of claim 8, wherein the lead makes an electrical connection with the plurality of rotatable contacts when the lead is inserted through the opening of the cover member.

11. The method of claim 8, further comprising attaching the lead connector to medical equipment.

12. The method of claim 8, wherein two or more rows of rotatable contacts are positioned below the array of receptacles within the bottom casing, such that when the lead is inserted into the lead connector via the opening on the cover member, the lead pushes against the two or more rows of rotatable contacts, electrically coupling the lead with the flexible circuit via the two or more rows of rotatable contacts and the plurality of electrical contacts of the flexible circuit.

13. The method of claim 12, wherein the given electrical contact of the lead makes contact with two or more rotatable contacts simultaneously.

14. A lead connector comprising:
a base member;
a flexible circuit disposed on the base member and comprising a plurality of electrical contacts;
a casing comprising a bottom casing and a cover member, wherein the bottom casing comprises an array of receptacles at least partially open to a surface of the flexible circuit and aligned with corresponding electrical contacts on the flexible circuit; and
an array of intermediary contacts mounted to locations on the flexible circuit corresponding to the array of receptacles, wherein the array of intermediary contacts are electrically coupled to the flexible circuit via the plurality of electrical contacts of the flexible circuit, and wherein the array of intermediary contacts comprises two or more rows of intermediary contacts positioned below the array of receptacles within the bottom casing, such that when the lead is inserted into the lead connector via the opening on the cover member, the lead pushes against the two or more rows of intermediary contacts, electrically coupling the lead with the flexible circuit via the two or more rows of intermediary contacts and the plurality of electrical contacts of the flexible circuit;

wherein when a lead is inserted through the lead connector via an opening on the cover member, the lead is in contact with the array of intermediary contacts, electrically coupling the lead with the flexible circuit via the array of intermediary contacts and the plurality of electrical contacts of the flexible circuit.

15. The lead connector of claim 14, wherein individual ones of the array of intermediary contacts comprises one or more of a ball contact, a radius pin, and a cylindrical pin.

16. The lead connector of claim 14, wherein the lead comprises an array of electrical contacts that aligns with the array of intermediary contacts.

17. The lead connector of claim 14, wherein a given electrical contact of the lead makes contact with two or more intermediary contacts simultaneously.

18. A method of using a lead connector for medical purposes comprising:
inserting a lead into an opening of the lead connector, the lead connector comprising:
a base member;
a flexible circuit disposed on the base member and comprising a plurality of electrical contacts;
a casing comprising a bottom casing and a cover member, wherein the bottom casing comprises an array of receptacles at least partially open to a surface of the flexible circuit and aligned with the plurality of electrical contacts on the flexible circuit, and wherein the cover member comprises an opening to receive the lead; and
an array of intermediary contacts mounted to locations on the flexible circuit corresponding to the array of receptacles, wherein the array of intermediary contacts are electrically coupled to the flexible circuit via the plurality of electrical contacts of the flexible circuit;
placing the lead into the opening on the lead connector till the lead pushes down on the array of intermediary contacts, wherein the lead has an array of electrical contacts, and wherein the lead makes an electrical connection with the array of intermediary contacts when the lead is inserted through the opening of the cover member; and
aligning the lead with the array of intermediary contacts, such that a given electrical contact of the lead is positioned to touch a corresponding intermediary contact.

19. The method of claim 18, wherein the array of intermediary contacts comprises two or more rows of intermediary contacts positioned below the array of receptacles within the bottom casing, such that when the lead is inserted into the lead connector via the opening on the cover member, the lead pushes against the two or more rows of intermediary contacts, electrically coupling the lead with the flexible circuit via the array of intermediary contacts and the plurality of electrical contacts of the flexible circuit.

20. The lead connector of claim 19, wherein the given electrical contact of the lead makes contact with two or more intermediary contacts of the array of intermediary contacts simultaneously.

21. A method of using a lead connector for medical purposes comprising:
inserting a lead into an opening of the lead connector, the lead connector comprising:
a base member;
a flexible circuit disposed on the base member and comprising a plurality of electrical contacts;
a casing comprising a bottom casing and a cover member, wherein the bottom casing comprises an array of receptacles at least partially open to a surface of the flexible circuit and aligned with the plurality of electrical contacts on the flexible circuit, and wherein the cover member comprises an opening to receive the lead; and
an array of intermediary contacts mounted to locations on the flexible circuit corresponding to the array of receptacles, wherein the array of intermediary contacts are electrically coupled to the flexible circuit via the plurality of electrical contacts of the flexible circuit, and wherein the array of intermediary contacts comprises two or more rows of intermediary contacts positioned below the array of receptacles within the bottom casing, such that when the lead is inserted into the lead connector via the opening on the cover member, the lead pushes against the two or more rows of intermediary contacts, electrically coupling the lead with the flexible circuit via the array of intermediary contacts and the plurality of electrical contacts of the flexible circuit;
placing the lead into the opening on the lead connector till the lead pushes down on the array of intermediary contacts, wherein the lead has an array of electrical contacts; and
aligning the lead with the array of intermediary contacts, such that a given electrical contact of the lead is positioned to touch a corresponding intermediary contact.

22. The lead connector of claim 21, wherein the given electrical contact of the lead makes contact with two or more intermediary contacts of the array of intermediary contacts simultaneously.

* * * * *